(12) United States Patent
Costabello et al.

(10) Patent No.: US 10,877,979 B2
(45) Date of Patent: Dec. 29, 2020

(54) DETERMINING EXPLANATIONS FOR PREDICTED LINKS IN KNOWLEDGE GRAPHS

(71) Applicant: Accenture Global Solutions Limited, Dublin (IE)

(72) Inventors: Luca Costabello, County Kildare (IE); Freddy Lecue, Dublin (IE)

(73) Assignee: Accenture Global Solutions Limited, Dublin (IE)

( * ) Notice: Subject to any disclaimer, the term of this patent is extended or adjusted under 35 U.S.C. 154(b) by 389 days.

(21) Appl. No.: 15/940,298

(22) Filed: Mar. 29, 2018

(65) Prior Publication Data
US 2019/0220524 A1    Jul. 18, 2019

Related U.S. Application Data

(63) Continuation-in-part of application No. 15/872,227, filed on Jan. 16, 2018, now Pat. No. 10,157,226.

(51) Int. Cl.
*G06F 16/2457* (2019.01)
*G06N 5/02* (2006.01)
(Continued)

(52) U.S. Cl.
CPC ...... *G06F 16/24578* (2019.01); *G06F 16/248* (2019.01); *G06F 16/9024* (2019.01); *G06N 5/02* (2013.01); *G06N 5/022* (2013.01)

(58) Field of Classification Search
CPC .............. G06F 16/24578; G06F 16/248; G06F 16/9024; G06N 5/02; G06N 5/022; G06N 5/04; G16H 50/70; G16H 70/00
See application file for complete search history.

(56) References Cited

U.S. PATENT DOCUMENTS 8,631,048 B1    1/2014 Davis et al.
10,496,691 B1 * 12/2019 Chen ....................... G06F 16/35
(Continued)

OTHER PUBLICATIONS

Hamaguchi et al., "Knowledge Transfer for Out-of-Knowledge-Base Entities: A Graph Neural Network Approach," https://arxiv.org/abs/1706.05674, arXiv preprint arXiv:1706.05674, Jun. 20, 2017, 7 pages.
(Continued)

*Primary Examiner* — David T. Brooks
(74) *Attorney, Agent, or Firm* — Harrity & Harrity, LLP

(57) ABSTRACT

A device receives a knowledge graph and an ontology for the knowledge graph, and receives a query for information associated with the knowledge graph. The device generates candidate responses to the query, and assigns scores to the candidate responses based on the knowledge graph. The device identifies a particular candidate response, of the candidate responses, based on the scores for the candidate responses, and determines, based on the knowledge graph, a neighborhood of the particular candidate response. The device generates knowledge graph embeddings for the neighborhood of the particular candidate response, and determines a particular neighborhood, with a smallest loss of quality, based on the knowledge graph embeddings. The device generates a reasoning graph based on the ontology and the particular neighborhood, and generates an explanation of the particular candidate response based on the reasoning graph. The device performs an action based the explanation of the particular candidate response.

20 Claims, 15 Drawing Sheets

(51) Int. Cl.
*G06F 16/248* (2019.01)
*G06F 16/901* (2019.01)

(56) References Cited

U.S. PATENT DOCUMENTS

| | | | |
|---|---|---|---|
| 2007/0143285 A1 | 6/2007 | Drumm et al. | |
| 2007/0233627 A1* | 10/2007 | Dolby | G06N 5/022 |
| | | | 706/45 |
| 2009/0012842 A1 | 1/2009 | Srinivasan et al. | |
| 2010/0121792 A1* | 5/2010 | Yang | G06F 16/9024 |
| | | | 706/12 |
| 2010/0281061 A1 | 11/2010 | Chen | |
| 2011/0307228 A1* | 12/2011 | Kasabov | G06Q 10/04 |
| | | | 703/2 |
| 2012/0239605 A1* | 9/2012 | Hohimer | G06N 5/046 |
| | | | 706/47 |
| 2013/0013645 A1 | 1/2013 | Dias et al. | |
| 2013/0297617 A1 | 11/2013 | Roy et al. | |
| 2014/0207802 A1* | 7/2014 | Raghavan | G06F 16/9024 |
| | | | 707/749 |
| 2014/0351261 A1* | 11/2014 | Aswani | G06F 16/9024 |
| | | | 707/741 |
| 2015/0095303 A1 | 4/2015 | Sonmez et al. | |
| 2016/0005197 A1 | 1/2016 | Walker et al. | |
| 2016/0026918 A1* | 1/2016 | Barbieri | H04L 67/22 |
| | | | 706/11 |
| 2016/0224645 A1 | 4/2016 | Dang | |
| 2016/0328253 A1 | 11/2016 | Majumdar | |
| 2016/0328443 A1 | 11/2016 | Abraham et al. | |
| 2017/0083507 A1 | 3/2017 | Ho et al. | |
| 2017/0091319 A1* | 3/2017 | Legrand | G06F 16/904 |
| 2017/0337268 A1 | 11/2017 | Ait-Mokhtar et al. | |
| 2017/0357905 A1* | 12/2017 | Rossi | G06N 5/022 |
| 2018/0082183 A1* | 3/2018 | Hertz | G06K 9/6259 |
| 2018/0341720 A1* | 11/2018 | Bhatia | G06N 5/003 |
| 2019/0073420 A1* | 3/2019 | Agapiev | G06F 16/9024 |
| 2019/0095806 A1* | 3/2019 | Martinez Canedo | |
| | | | G06F 16/9024 |
| 2019/0286754 A1* | 9/2019 | Leskovec | G06F 16/182 |

OTHER PUBLICATIONS

Bordes et al., "Translating Embeddings for Modeling Multi-relational Data," Advances in neural information processing systems, 2787-2795, 2013, 9 pages.

Trouillon et al., "Complex Embeddings for Simple Link Prediction," International Conference on Machine Learning, arXiv:1606.06357v1 [cs.AI], 2071-2080, Jun. 20, 2016, 12 pages.

Yang et al., "Embedding Entities and Relations for Learning and Inference in Knowledge Bases," arXiv preprint arXiv:1412.6575, Aug. 29, 2015, 12 pages.

Nickel et al.. "A Review of Relational Machine Learning for Knowledge Graphs," Proceedings of the IEEE 104.1, arXiv:1503.00759v3, 11-33, Sep. 28, 2015, 23 pages.

Cai et al., "A Comprehensive Survey of Graph Embedding: Problems, Techniques and Applications," arXiv preprint arXiv:1709.07604, Jan. 3, 2018, 20 pages.

* cited by examiner

US 10,877,979 B2

DETERMINING EXPLANATIONS FOR PREDICTED LINKS IN KNOWLEDGE GRAPHS

RELATED APPLICATION

This application is a continuation-in-part (CIP) of U.S. patent application Ser. No. 15/872,227, filed on Jan. 16, 2018, the content of which is incorporated by reference herein in its entirety.

BACKGROUND

A knowledge graph or an ontology includes types, properties, and interrelationships between entities that exist in a domain of discourse. A knowledge graph compartmentalizes variables needed for some set of computations, and establishes relationships between the variables. The fields of artificial intelligence, systems engineering, software engineering, biomedical informatics, library science, enterprise bookmarking, and/or the like create knowledge graphs or ontologies to limit complexity and organize information. A knowledge density of a knowledge graph is an average number of attributes and binary relations issued from a given entity, and is measured in facts per entity.

SUMMARY

According to some implementations, a device may include one or more memories, and one or more processors, communicatively coupled to the one or more memories, to receive a knowledge graph and an ontology for the knowledge graph, and receive a query for information associated with the knowledge graph. The one or more processors may generate candidate responses to the query based on the knowledge graph, and may assign scores to the candidate responses based on the knowledge graph. The one or more processors may identify a particular candidate response, of the candidate responses, based on the scores for the candidate responses, and may determine, based on the knowledge graph, a neighborhood of the particular candidate response. The one or more processors may generate knowledge graph embeddings for the neighborhood of the particular candidate response, and may determine a particular neighborhood, with a smallest loss of quality, based on the knowledge graph embeddings. The one or more processors may generate a reasoning graph based on the ontology and the particular neighborhood, and may generate an explanation of the particular candidate response based on the reasoning graph. The one or more processors may perform an action based the explanation of the particular candidate response.

According to some implementations, a non-transitory computer-readable medium may store instructions that include one or more instructions that, when executed by one or more processors, cause the one or more processors to receive a knowledge graph generated based on training data and an ontology for the training data, where the training data may include information associated with a subject of the ontology. The one or more instructions may cause the one or more processors to receive a query for information associated with the knowledge graph, and generate candidate responses to the query based on the knowledge graph. The one or more instructions may cause the one or more processors to identify a particular candidate response, of the candidate responses, based on scoring the candidate responses based on the knowledge graph, and determine, based on the knowledge graph, a neighborhood of the particular candidate response. The one or more instructions may cause the one or more processors to generate knowledge graph embeddings for the neighborhood of the particular candidate response, and identify, based on the knowledge graph embeddings, a portion of the neighborhood with a smallest loss of quality. The one or more instructions may cause the one or more processors to generate a reasoning graph based on the ontology and the portion of the neighborhood, and generate an explanation of the particular candidate response based on the reasoning graph. The one or more instructions may cause the one or more processors to perform one or more actions based the explanation of the particular candidate response.

According to some implementations, a method may include receiving, by a device, a knowledge graph generated based on training data and an ontology for the training data, and receiving, by the device, a query for information associated with the knowledge graph. The method may include generating, by the device, candidate responses to the query based on the knowledge graph, and assigning, by the device, scores to the candidate responses based on the knowledge graph. The method may include identifying, by the device, a particular candidate response, of the candidate responses, based on the scores for the candidate responses, and determining, by the device and based on the knowledge graph, a neighborhood of the particular candidate response. The method may include generating, by the device, knowledge graph embeddings for the neighborhood of the particular candidate response, where the knowledge graph embeddings may include points in a k-dimensional metric space. The method may include identifying, by the device and based on the knowledge graph embeddings, a portion of the neighborhood with a smallest loss of quality, and generating, by the device, a reasoning graph based on the ontology and the portion of the neighborhood, where the reasoning graph may include two or more different levels of abstraction associated with nodes that represent concepts and links that represent relations between the concepts. The method may include generating, by the device, an explanation of the particular candidate response based on the reasoning graph, and performing, by the device, at least one action based the explanation of the particular candidate response.

DETAILED DESCRIPTION

The following detailed description of example implementations refers to the accompanying drawings. The same reference numbers in different drawings may identify the same or similar elements.

A knowledge graph is an expressive, schema-rich, domain-independent data modeling paradigm that is particularly well-suited to model relations between entities. In machine learning, knowledge graph embedding models predict existences of labeled links between entities. Such predictions are a result of operations between points (e.g., known as embeddings) in a metric space. The embeddings are learned from the entire knowledge graph during training of the knowledge graph. However, a knowledge graph embedding model is unable to predict links associated with a new unknown entity. In such cases, an embedding model of the knowledge graph cannot predict the links because the unknown entity is not known during the training of the knowledge graph, and the embedding model did not learn a corresponding representation in the metric space. Some techniques handle unknown entities by completely retraining the knowledge graph. Unfortunately, such techniques consume significant time and resources (e.g., processors, memory, and/or the like) in order to retrain the knowledge graph. Furthermore, the embedding model of the knowledge graph relies on architectures that are ill-suited to provide effective explanations of predicted links to end users.

Some implementations described herein provide a prediction platform that determines explanations for predicted links in knowledge graphs. For example, the prediction platform may receive a knowledge graph generated based on training data and an ontology for the training data, and may receive a query for information associated with the knowledge graph. The prediction platform may generate candidate responses to the query based on the knowledge graph, and may score the candidate responses based on the knowledge graph. The prediction platform may determine, based on the knowledge graph, a neighborhood of the particular candidate response, and may generate knowledge graph embeddings for the neighborhood of the particular candidate response. The prediction platform may determine a particular neighborhood with a smallest loss of quality based on the knowledge graph embeddings. The prediction platform may generate a reasoning graph based on the ontology and the particular neighborhood, and may generate an explanation of the particular candidate response based on the reasoning graph.

Figure 1A:
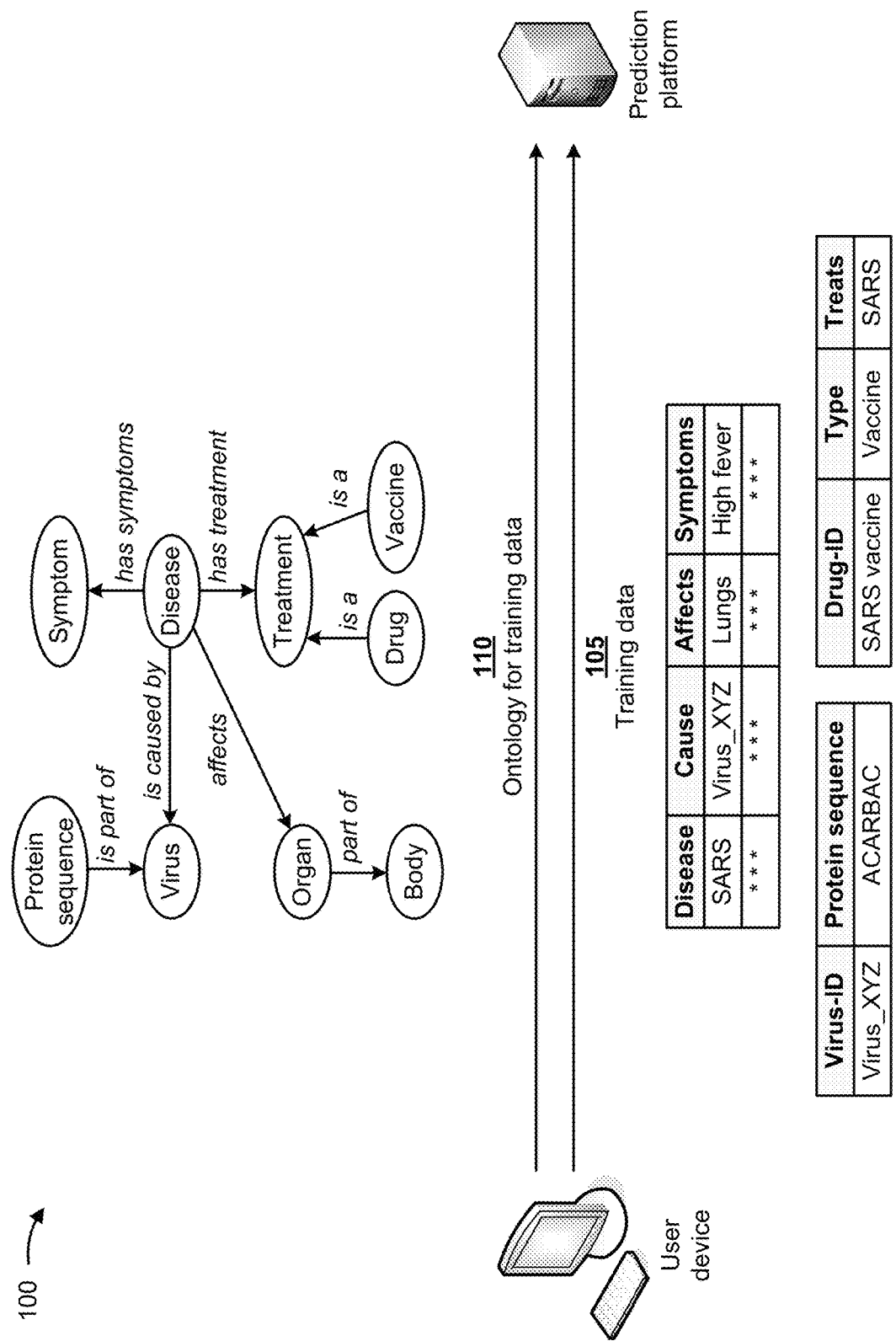
FIGS. 1A-1L are diagrams of an overview of an example implementation described herein.

FIGS. 1A-1L are diagrams of an overview of an example implementation 100 described herein. As shown in FIG. 1A, a user device may be associated with a prediction platform. As shown in FIG. 1A, and by reference number 105, a user of the user device (e.g., via a user interface provided to the user) may cause the user device to provide, to the prediction platform, training data for training a knowledge graph associated with a particular disease (e.g., severe acute respiratory syndrome (SARS)). As further shown in FIG. 1A, and by reference number 110, the user may cause the user device to provide, to the prediction platform, an ontology for the training data. In some implementations, the training data and the ontology may not be stored in the user device, but the user device may cause the training data and the ontology to be provided from a resource, storing the training data and the ontology, to the prediction platform. In some implementations, the training data and the ontology may be stored in the prediction platform. In some implementations, although FIGS. 1A-1L relate to healthcare and biomedical domains, the prediction platform may be used with any type of domain and may be domain agnostic.

In some implementations, the training data may include information associated with a subject of the ontology. For example, example implementation 100 relates to an ontology associated with the SARS disease. Thus, the training data may include data associated with the SARS disease that is received from relationship database management systems (RDBMS), comma-separated values (CSV) data stores, and/or the like. As shown in FIG. 1A, the training data may include data indicating a disease (e.g., SARS), a cause of the disease (e.g., virus_XYZ), what organ the disease affects (e.g., lungs), symptoms of the disease (e.g., high fever), a virus identifier (e.g., virus_XYZ), a protein sequence associated with the virus (e.g., ACARBAC), a drug identifier associated with a drug that treats the disease (e.g., SARS vaccine), a drug type (e.g., vaccine), what the drug treats (e.g., SARS), and/or the like.

The ontology (e.g., resource description framework (RDF) ontology, web ontology language (OWL), and/or the like) for the training data may include classes, types, properties, and interrelationships (e.g., relations) between data of the training data. For example, as shown in FIG. 1A, the ontology may include nodes that represent concepts related to a disease, and edges or links that show interrelationships (e.g., relations) between the concepts related to the disease. As shown, a disease node may connect to a symptom node, and a link between the nodes may indicate that the disease has symptoms. The disease node may connect to a treatment node, and a link between the nodes may indicate that the disease has a treatment. The disease node may connect to a virus node, and a link between the nodes may indicate that the disease is caused by the virus. The disease node may also connect to an organ node, and a link between the nodes may indicate that the disease affects the organ. The virus node may connect to a protein sequence node, and a link between the nodes may indicate that the protein sequence is part of the virus. The organ node may connect to a body node, and a link between the nodes may indicate that the organ is part of the body. The treatment node may connect to a drug node and a vaccine node, and the links between the nodes may indicate that the drug and the vaccine are treatments for the disease.

Figure 1B:
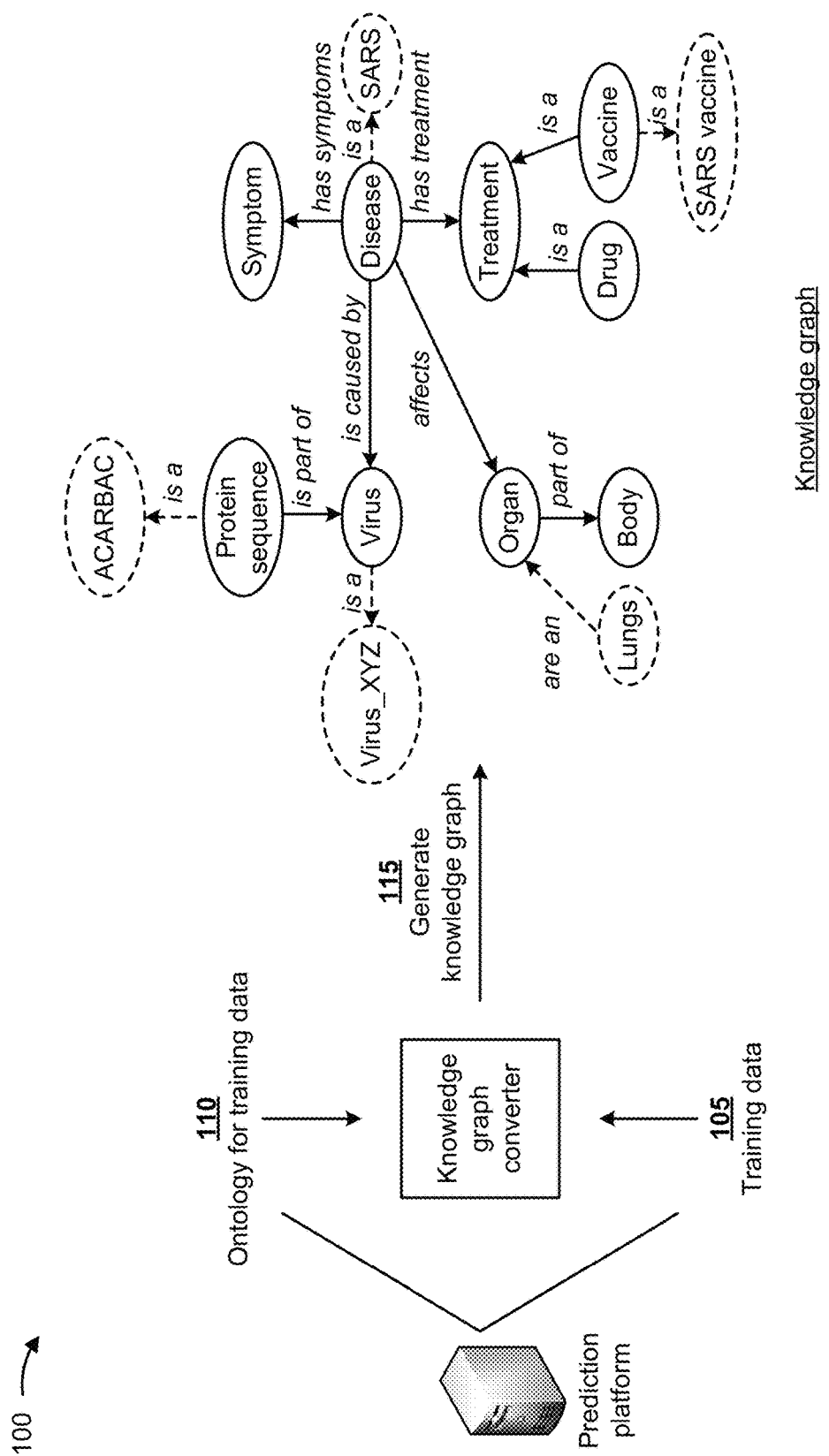

As shown in FIG. 1B, and by reference numbers 105 and 110, the training data and the ontology may be provided to a knowledge graph converter of the prediction platform. In some implementations, the knowledge graph converter may receive the training data and the ontology, and may convert the training data from a format received by the prediction platform (e.g., a relational database format, a CSV format, and/or the like) into another format (e.g., a resource descriptive framework (RDF) format). In some implementations, the knowledge graph converter may aggregate the converted training data so that the knowledge graph converter may process the aggregated data.

As further shown in FIG. 1B, and by reference number 115, the knowledge graph converter may generate a knowledge graph based on the training data and the ontology (e.g., based on the converted and aggregated training data and the ontology). In some implementations, the knowledge graph converter may utilize a schema matching technique to align the training data and to integrate the aligned training data into the ontology (e.g., to generate the knowledge graph). The schema matching technique may include determining semantic correspondences between elements of two schemas (e.g., the training data and the ontology). In some implementations, the schema matching technique may analyze and compare the schema to determine correspondences among concepts and to detect possible conflicts. Once the conflicts are detected, the schema matching technique may resolve the conflicts so that merging of the schemas is possible. Once the conflicts are resolved, the schema matching technique may merge the schemas. In some implementations, the schema matching technique may include a schema-level matching technique (e.g., that considers schema information and not instance data), an instance-level matching technique (e.g., that use instance-level data to gather insights into contents and meanings of schema elements), a hybrid matching technique (e.g., that combines several matching techniques to determine match candidates based on multiple criteria or information sources), a reusing matching information technique (e.g., that reuses previous matching information as auxiliary information for future matching tasks), and/or the like.

In some implementations, the knowledge graph converter may utilize other techniques to align the training data and to integrate the aligned training data into the ontology (e.g., to generate the knowledge graph), such as machine learning techniques, and/or the like.

As further shown in FIG. 1B, the knowledge graph may include the training data integrated within the ontology as nodes that represent concepts, and edges or links that show interrelationships (e.g., relations) between the concepts. For example, in addition to the information conveyed by the ontology, the knowledge graph may indicate that SARS is an instance of Disease, that ACARBAC is an instance of a protein sequence, that virus_XYZ node is an instance of a Virus, that lungs are an instance of an Organ, and that SARS vaccine is an instance of Vaccine. Thus, the knowledge graph may indicate that SARS is a disease with a vaccine treatment by the SARS vaccine.

Figure 1C:
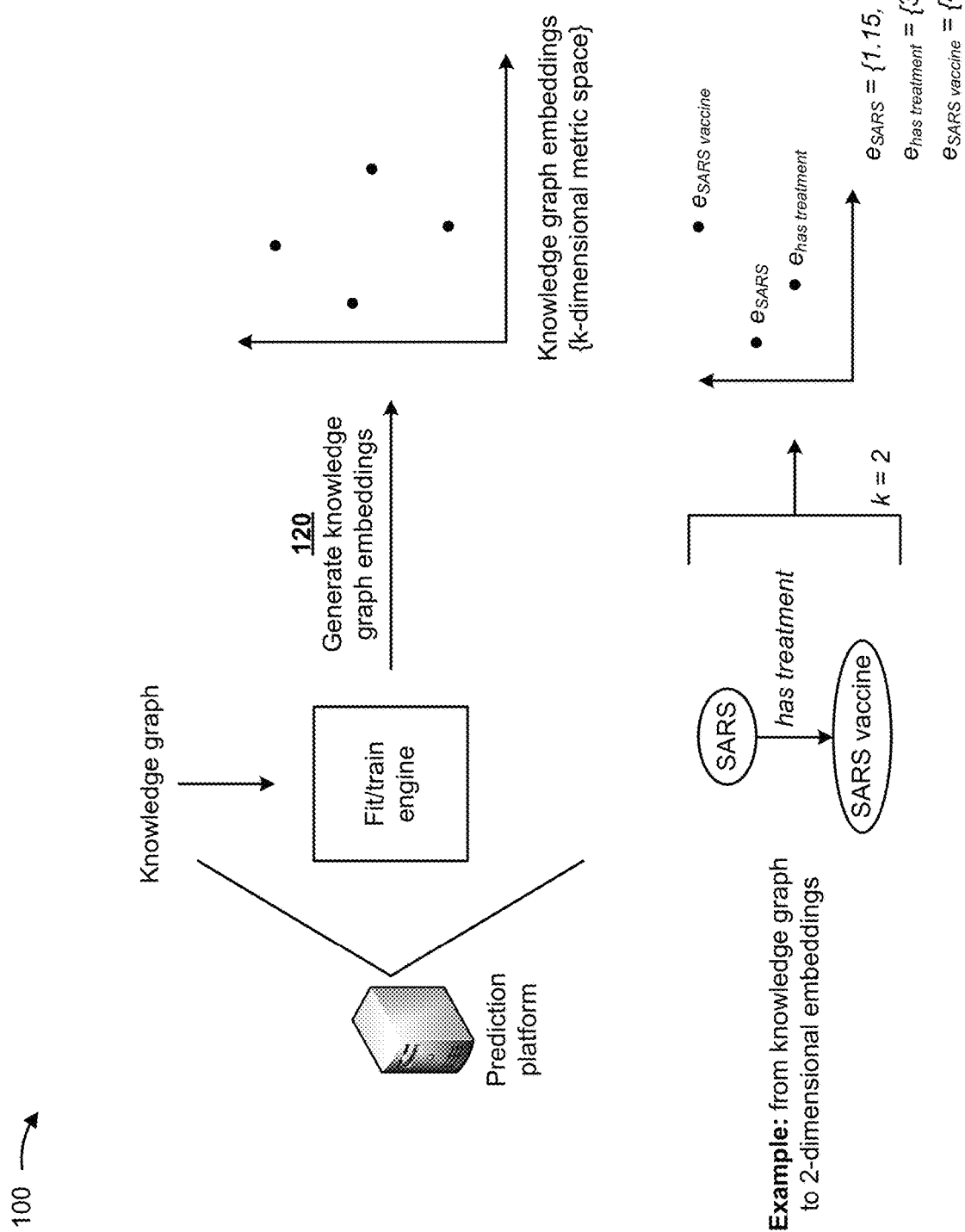

As shown in FIG. 1C, a fit/train engine, of the prediction platform, may receive the knowledge graph. In some implementations, the knowledge graph may be serialized into a list of statements, and the list of statements may be received by the fit/train engine. As further shown in FIG. 1C, and by reference number 120, the fit/train engine may generate knowledge graph embeddings based on the knowledge graph. In some implementations, the knowledge graph embeddings may include points in a k-dimensional metric space, and may provide latent semantic representations for structured knowledge in the knowledge graph. In some implementations, the knowledge graph embeddings may enable direct explicit relational inferences among entities via simple calculation of embedding vectors, and may be effective at highlighting key concepts underlying sophisticated human language.

In some implementations, the fit/train engine may convert entities (e.g., nodes) and relations (e.g., links or edges) of the knowledge graph into points in a k-dimensional metric space. For example, as shown in FIG. 1C, the knowledge graph embeddings may include points in a k-dimensional metric space (e.g., shown as a graph in two dimensions for simplicity). In some implementations, the fit/train engine may minimize a loss function to learn model parameters that best discriminate positive statements from negative statements. In such implementations, the loss function may include a function that maps a statement onto a real number that represents the likelihood of that statement to be true. In such implementations, the loss function may include a pairwise margin-based loss function, a negative log-likelihood loss function, and/or the like. In some implementations, the fit/train engine may assign scores to statements of the knowledge graph in order to aid the loss function in determining how well the knowledge graph tells positive statements from negative statements. In some implementations, the fit/train engine may minimize the loss function in order to determine optimal parameters of the knowledge graph (e.g., the knowledge graph embeddings).

As further shown in FIG. 1C, an example knowledge graph in two dimensions (e.g., k=2) may indicate that a SARS vaccine is a treatment for SARS. In such an example, the fit/train engine may generate three knowledge graph embeddings (e.g., points) on a two-dimensional metric space. As further shown, the three points may include a point representing SARS (e.g., located at {1.15, 3.45}), a point representing that SARS has a treatment (e.g., located at {3.25, 1.15}), and a point representing the SARS vaccine (e.g., located at {4.82, 5.62}).

Figure 1D:
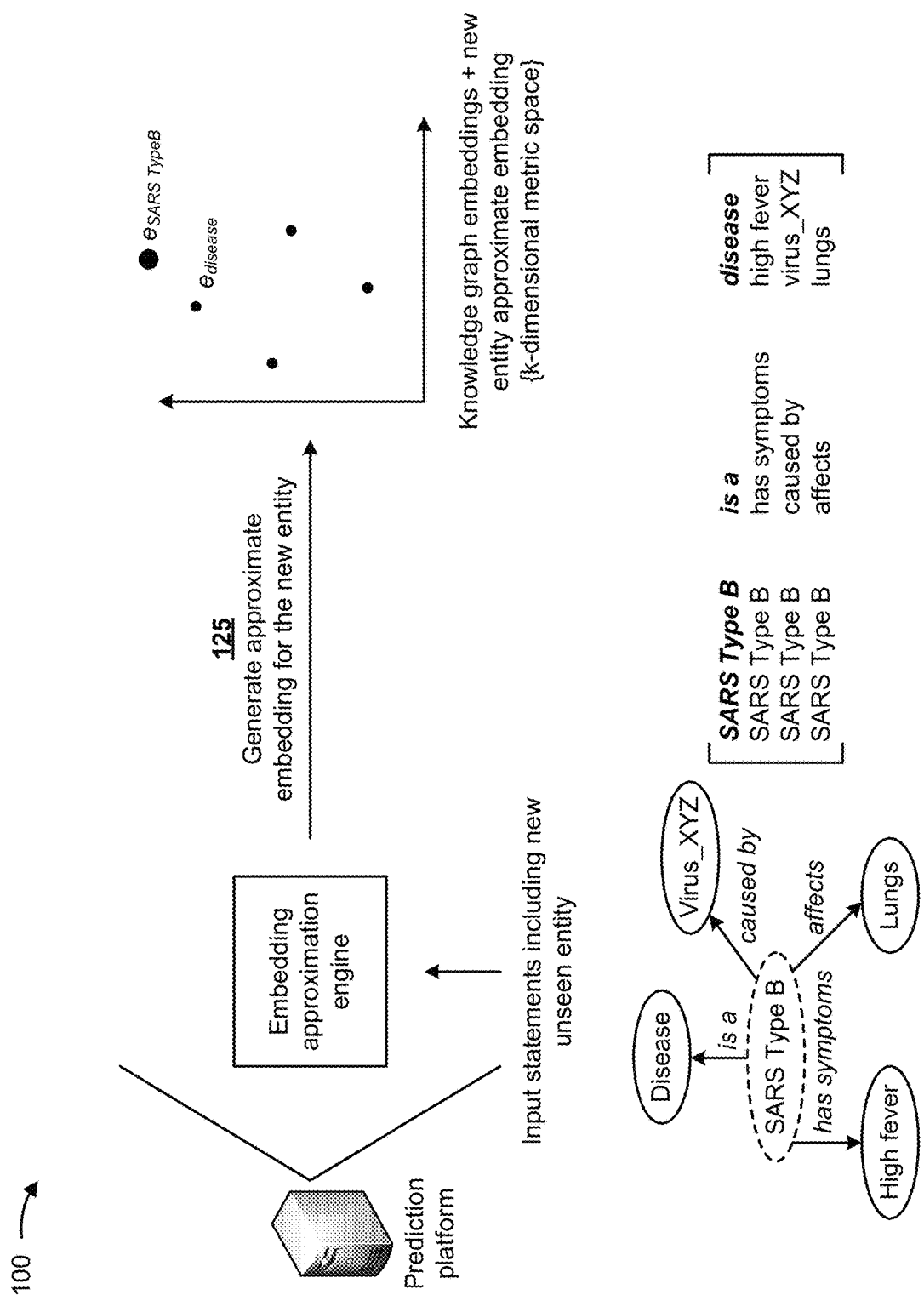

As shown in FIG. 1D, assume that the prediction platform receives (e.g., from the user device) new statements, indicating among all that SARS Type B is a disease. As further shown, such input may include ontology-related statements. In some implementations, the ontology may include a SARS Type B node that connects to a disease node, and a link between the nodes may indicate that SARS Type B is a disease. The SARS Type B node may connect to a virus_XYZ node, and a link between the nodes may indicate that SARS Type B is caused by virus_XYZ. The SARS Type B node may connect to a high fever node, and a link between the nodes may indicate that SARS Type B has a high fever as a symptom. The SARS Type B node may connect to a lungs node, and a link between the nodes may indicate that SARS Type B affects the lungs. In some implementations, a serialized representation of the ontology-related statements may indicate the same information in a different format.

Previously, such new statements were unable to be scored because at least one unseen entity was not included in the training data, the original knowledge graph, and the knowledge graph embeddings, i.e., SARS Type B. However, as further shown in FIG. 1D, and by reference number 125, an embedding approximation engine, of the prediction platform, may receive the new unseen entity, and may generate knowledge graph embeddings revised with the embedding of the unseen entity.

In some implementations, the embedding approximation engine may approximate an embedding for the new entity based on a weight (e.g., >1), the average of the embeddings of the entities that belong to the schema (e.g., the ontology), and are related to the new entity (e.g., the entity "disease" shown in bold and italics in FIG. 1D), and the average of the embeddings of entities that are in the ontology, are related to the new entity but that do not belong to the schema, (e.g., the remaining entities that belong to the statements shown in FIG. 1D, other than the entity "disease").

In some implementations, the embedding approximation engine may approximate an embedding for the new entity ($e_{new}$ or $e_{SARS\_TypeB\_is\_a\_disease}$) based on the following equation:

$$e_{new} = \alpha \frac{1}{|\eta_s|} \sum_{s}^{|\eta_s|} e_s + \frac{1}{|\eta_e|} \sum_{i}^{|\eta_e|} e_i,$$

where $\alpha$ may correspond to the weight (e.g., >1), $$\frac{1}{|\eta_s|} \sum_{s}^{|\eta_s|} e_s$$

may correspond to the average of the entity embeddings that are related to the new entity, and are related to the schema, $$\frac{1}{|\eta_e|} \sum_{i}^{|\eta_e|} e_i$$

may correspond to the average of the entity embeddings that are related to the new, unseen entity, and are not related to the schema, $\eta_s$ may correspond to the entities that are related to the new, unseen entity, and are related to the schema, $\eta_e$ may correspond to all other entities that are related to the new entity, and are not related to the schema, $e_s$ may correspond to an embedding of an entity in the schema, and $e_i$ may correspond to an embedding of an entity not in the schema. Thus, the embedding approximation engine may apply more weight to the entities that are related to the schema than to the entities that are not related to the schema.

As further shown in FIG. 1D, the revised knowledge graph embeddings may include points in the k-dimensional metric space (e.g., shown as a graph in two dimensions for simplicity), and may include points (e.g., embeddings) calculated for the new entity (e.g., $e_{SARS\_TypeB}$) and for the disease node (e.g., $e_{disease}$).

Figure 1E:
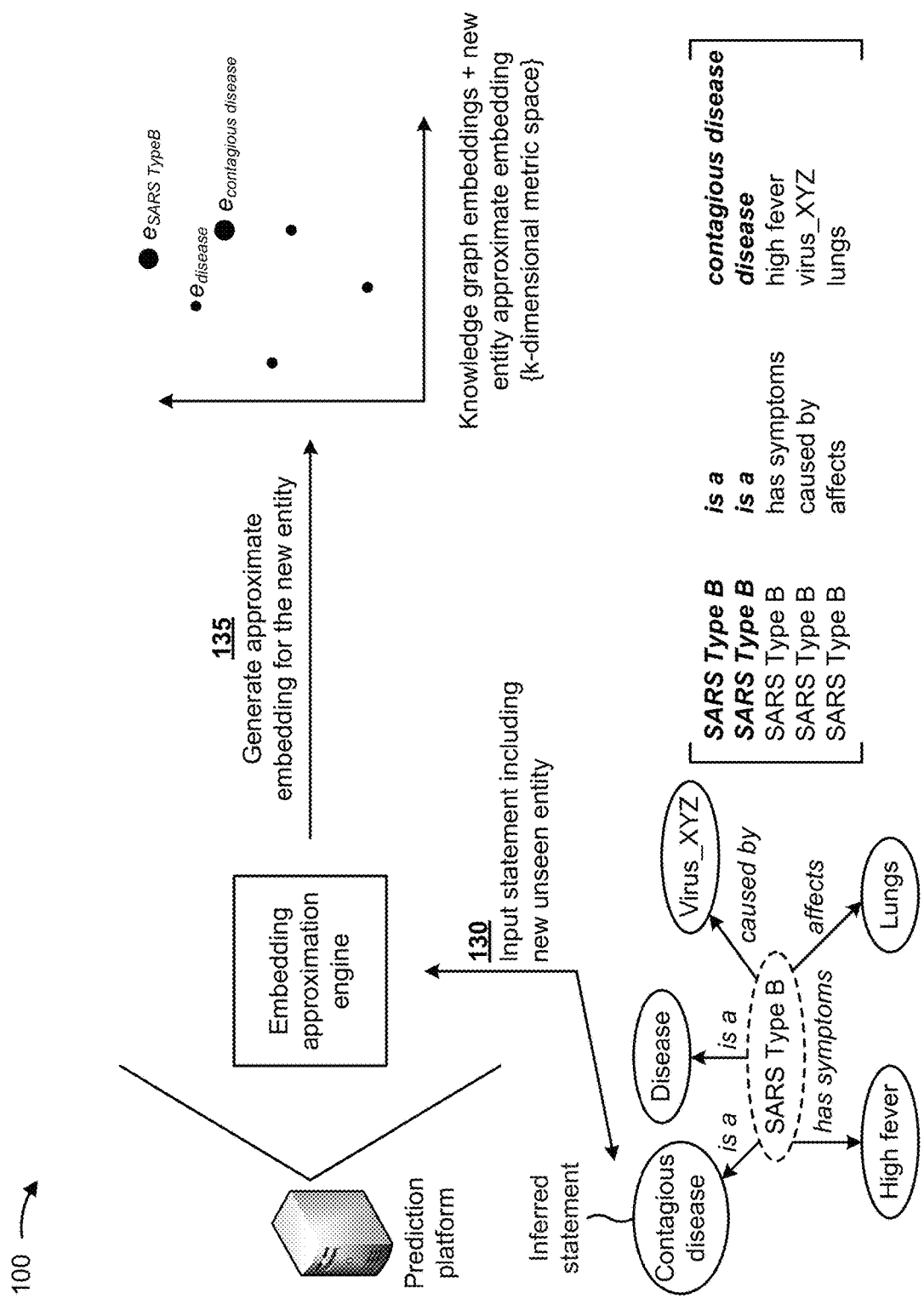

With reference to FIG. 1E, in some implementations, the prediction platform may expand a number of schema-related entities utilized by the embedding approximation engine, by utilizing reasoning techniques (e.g., techniques that generate conclusions from available knowledge using logical techniques such as deduction and induction) to infer a new entity (e.g., SARS Type B is a contagious disease). In such implementations, the prediction platform may modify $\eta_s$ (e.g., which may correspond to the entities that are in the ontology) based on the following equation:

$$\eta_s = \eta_s^{original} + \eta_s^{inferred},$$

where $\eta_s^{original}$ may correspond to $\eta_s$ described above in connection with FIG. 1D (e.g., which may correspond to the entities that are in the ontology), $\eta_s^{inferred}$ may correspond to the inferred entities (i.e., entities that belong to inferred new statements), and $\eta_s$ may correspond to the expanded set of entities related to the new, unseen entity.

As further shown in FIG. 1E, and by reference number 130, the prediction platform may provide, to the embedding approximation engine, the new statements indicating, among all, that SARS Type B is a contagious disease. As further shown, the new entity may include an ontology and a serialized representation of the ontology. In some implementations, the ontology may include the ontology described above in connection with FIG. 1D. The SARS Type B node may also be part of a new inferred statement (e.g., SARS Type B is a contagious disease). In some implementations, the serialized representation of the ontology may indicate the same information as the ontology in a different format, but may also include the statement "SARS Type B is a contagious disease." The statements "SARS Type B is a disease" and "SARS Type B is a contagious disease" are shown in bold and italics in FIG. 1E to indicate that these statements are related to the schema, while remaining statements are not related to the schema.

As further shown in FIG. 1E, and by reference number 135, the embedding approximation engine, of the prediction platform, may receive the new statements, and may generate revised knowledge graph embeddings for the unseen entity included in the new statements, in the manner described above in connection with FIG. 1D. As further shown in FIG. 1E, the revised knowledge graph embeddings may include points in the k-dimensional metric space (e.g., shown as a graph in two dimensions for simplicity), and may include a point (e.g., an embedding) calculated for the new, unseen entity (e.g., $e_{contagious\_disease}$).

Figure 1F:
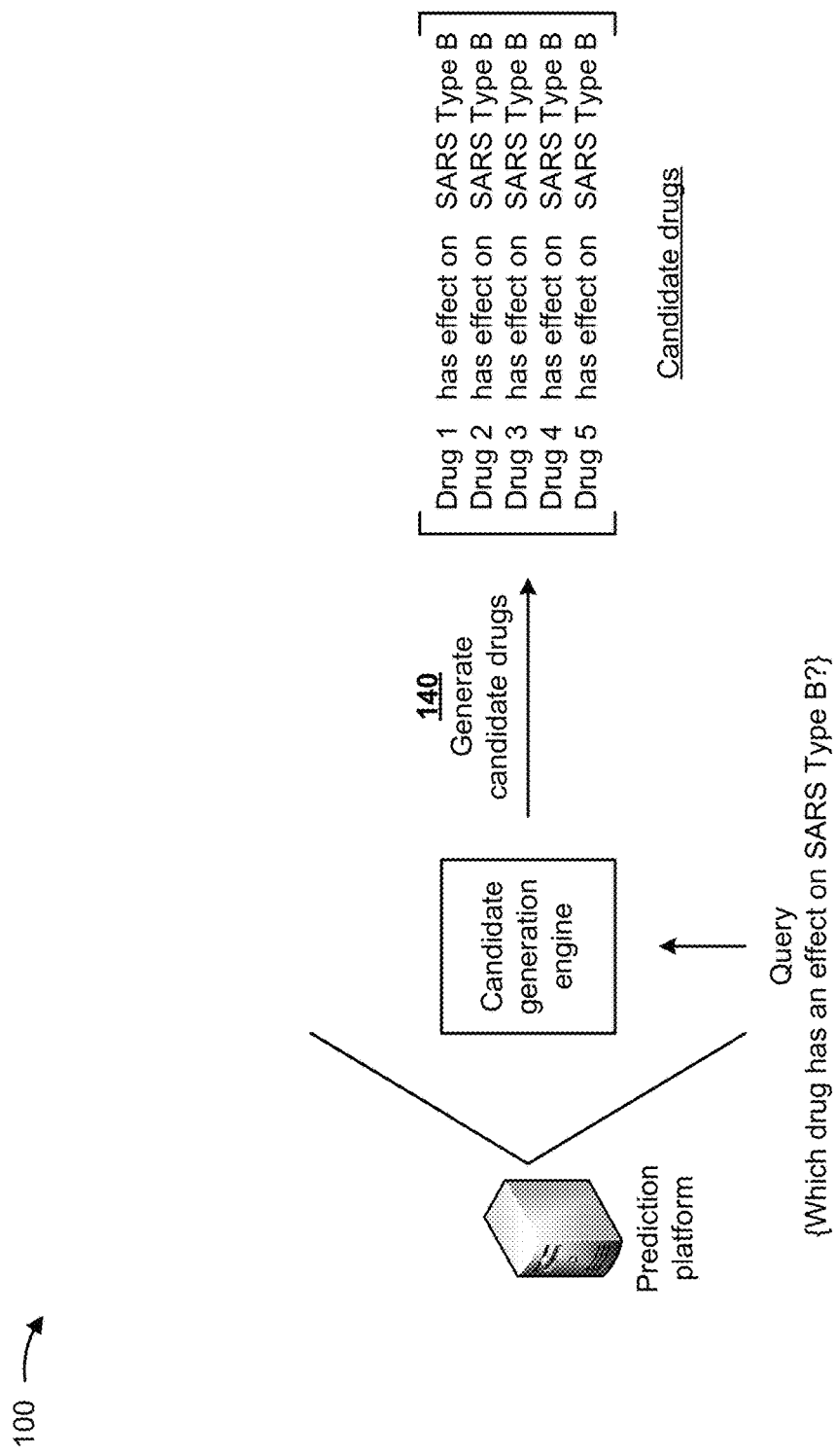

As shown in FIG. 1F, a candidate generation engine, of the prediction platform, may receive a query to identify a drug that has an effect on SARS Type B. In some implementations, the candidate generation engine may analyze the query based on the knowledge graph to determine drugs that have an effect on SARS. As further shown in FIG. 1F, and by reference number 140, the candidate generation engine may generate information indicating candidate drugs based on the query and based on the analysis with the knowledge graph. As further shown in FIG. 1F, the information indicating the candidate drugs may be generated in a particular format (e.g., a statements serialization or format) and may indicate that drugs 1-5 are potential candidates as having an effect on SARS Type B.

Figure 1G:
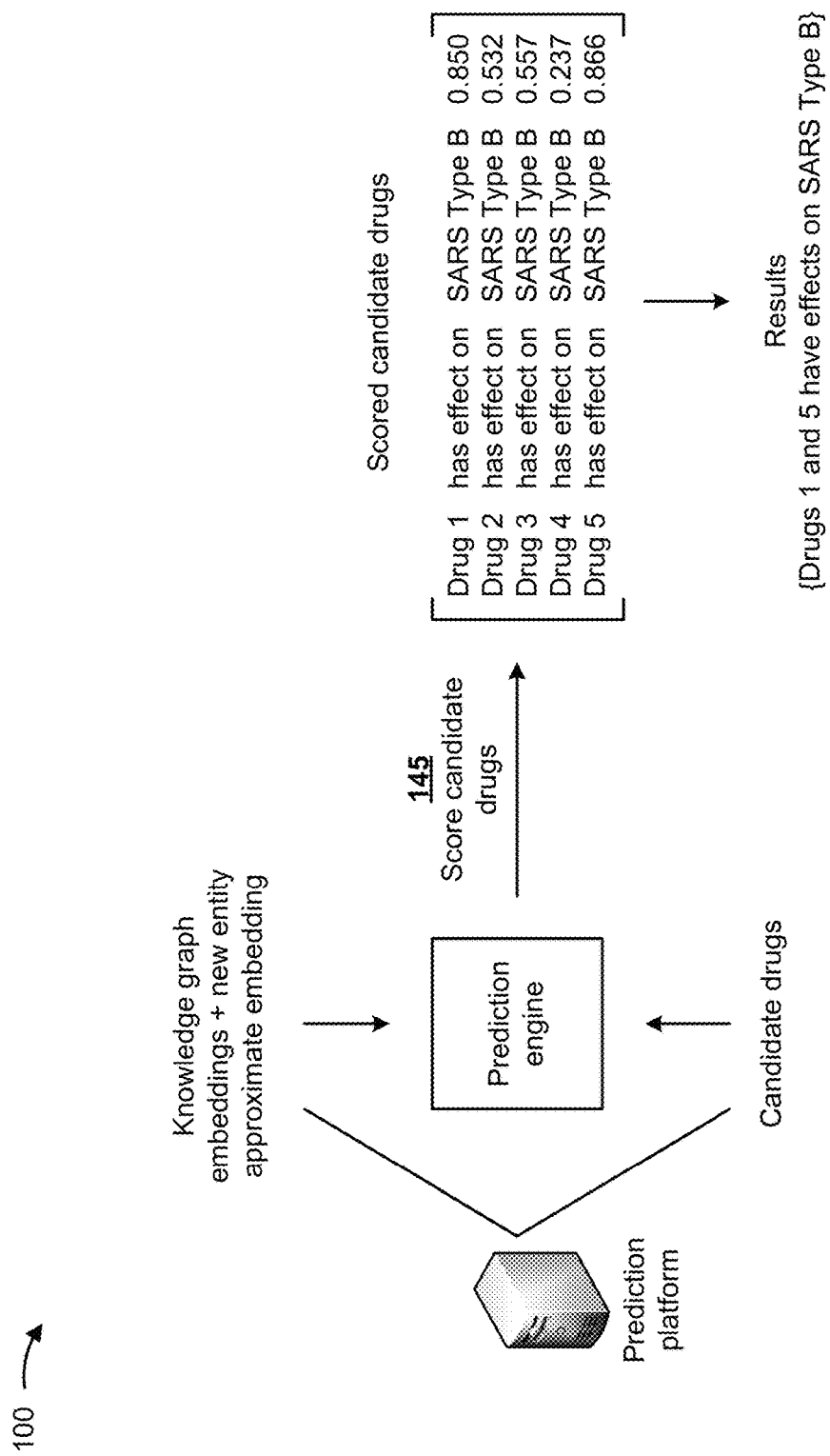
Figure 1H:
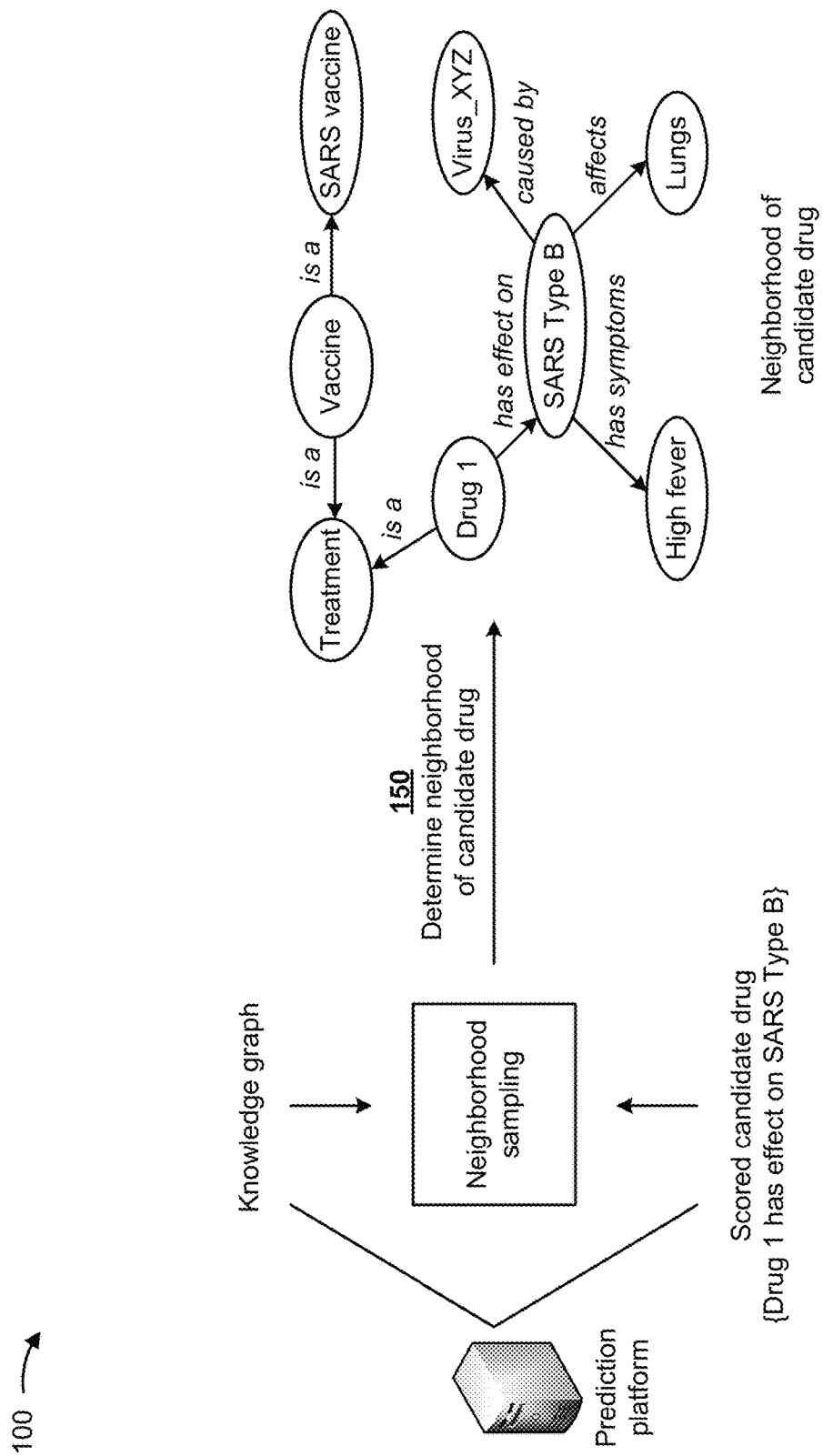
Figure 1I:
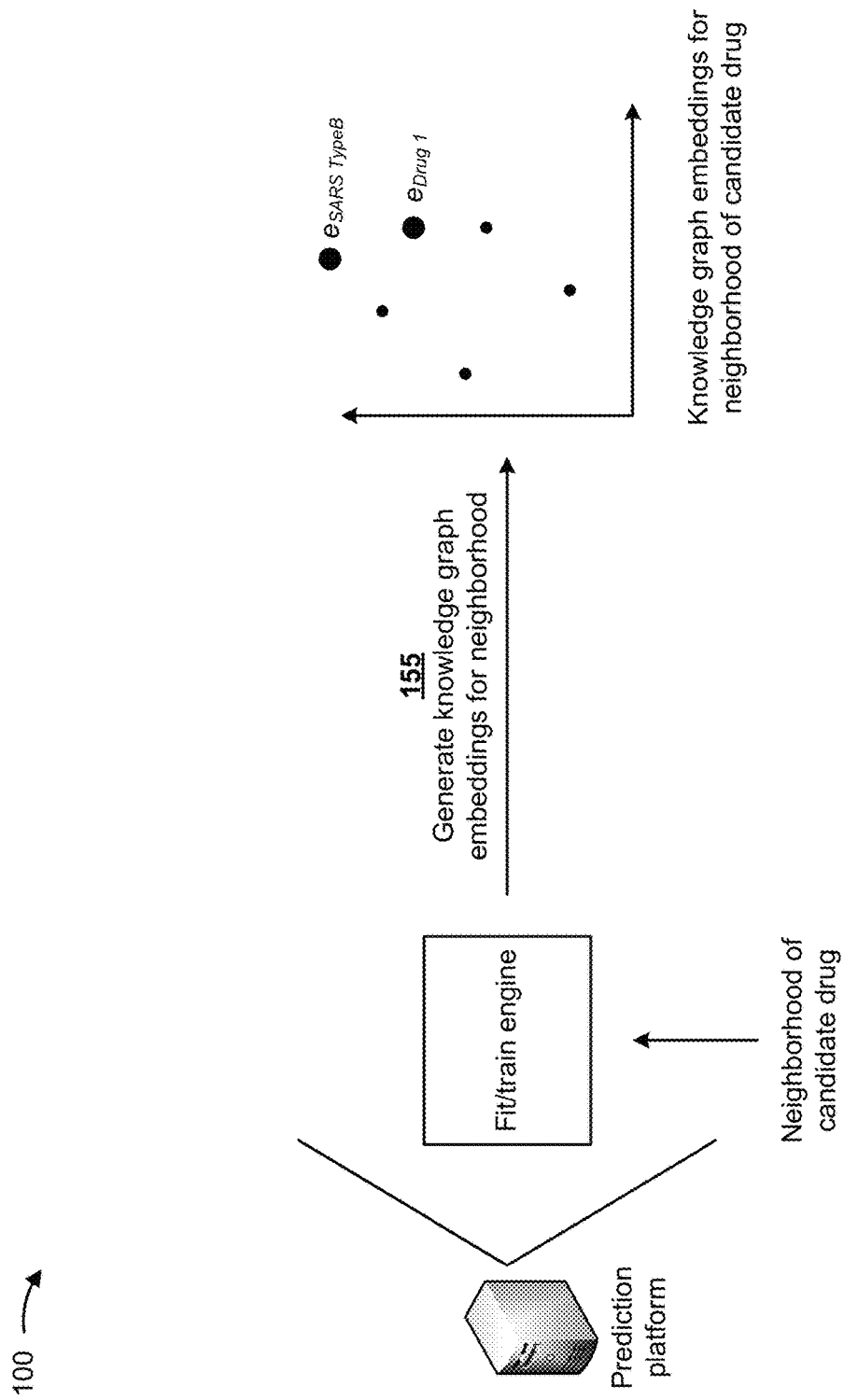

As shown in FIG. 1G, a prediction engine, of the prediction platform, may receive the revised knowledge graph embeddings (e.g., described above in connection with to FIG. 1E) and the candidate drugs (e.g., described above in connection with FIG. 1F). In some implementations, and as shown by reference number 145 in FIG. 1G, the prediction engine may score the candidate drugs based on the revised knowledge graph embeddings. In such implementations, the prediction engine may utilize a relational learning model (e.g., TransE, RESCAL, ComplEx, DistMult, HolE, and/or the like) to determine values associated with the candidate statements (e.g., scores). The prediction engine may then utilize the values to calculate the probability estimates for the candidate drugs.

As further shown in FIG. 1G, the prediction engine may provide the scored candidate drugs in a particular format. In some implementations, the scored candidate drugs may include the information included in the candidate drugs and may also include the scores for the candidate drugs (e.g., drug 1 has a score of 0.850, drug 2 has a score of 0.532, drug 3 has a score of 0.557, drug 4 has a score of 0.237, and drug 5 has a score of 0.866).

As further shown in FIG. 1G, the prediction engine may calculate results for the scored candidate drugs. In some implementations, the prediction engine may utilize a predetermined threshold for a score (e.g., 0.80) to calculate the results, where if a candidate drug has a score that satisfies the predetermined threshold, the prediction engine may output that candidate drug as being a drug that has an effect on SARS Type B. For example, since drugs 1 and 5 have scores greater than the predetermined threshold, the prediction engine may output drug 1 and/or drug 5 as having an effect on SARS Type B. In some implementations, the prediction platform may provide the scored candidate drugs and/or the results to the user device, and the user device may display the scored candidate drugs and/or the results to a user of the user device (e.g., via a user interface).

Figure 1J:
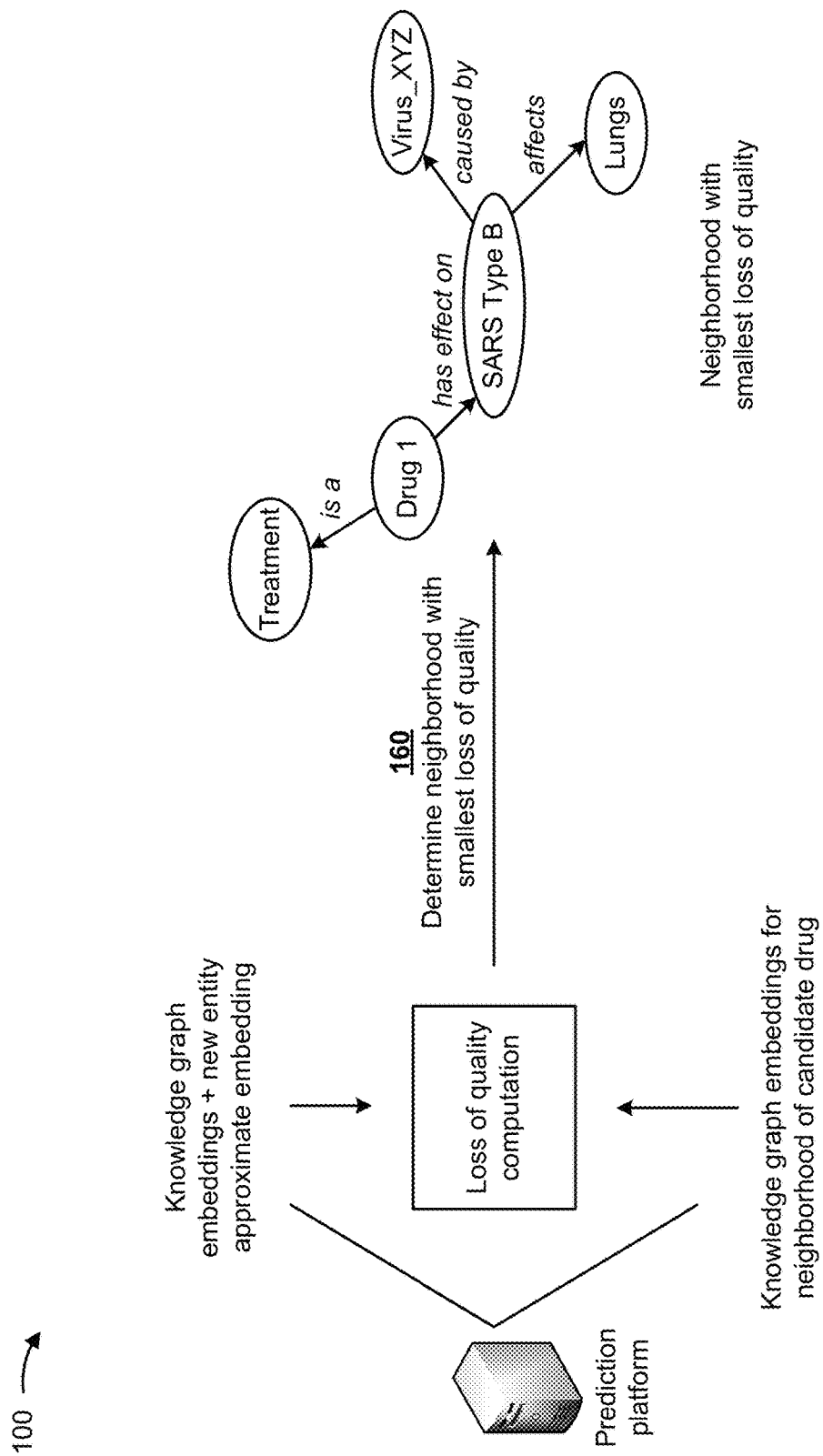
Figure 1K:
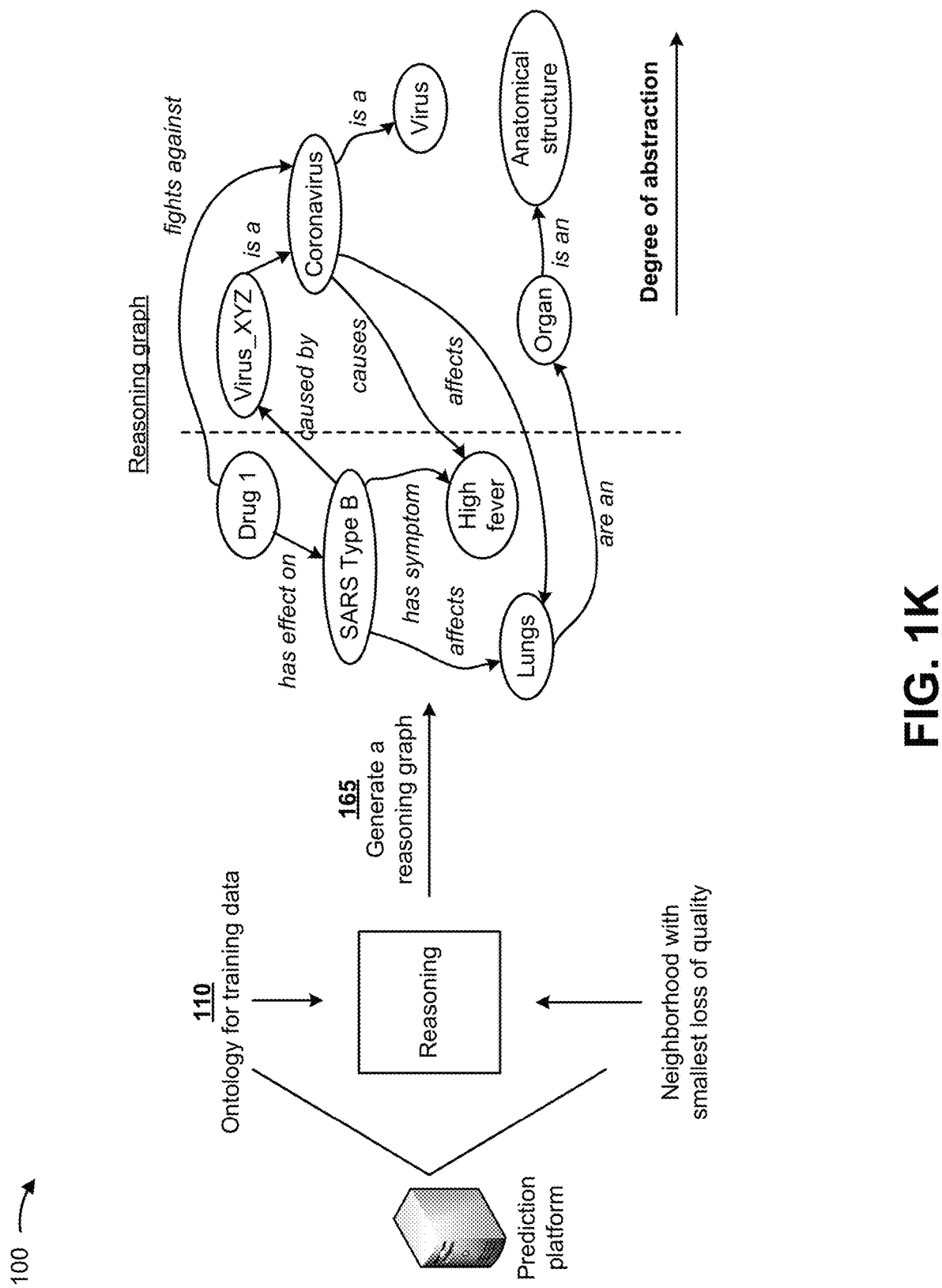

In some implementations, the prediction platform may perform a variety of actions based on the identified candidate response. For example, the prediction platform may automatically order the candidate drugs if there is an uptick in SARS Type B; automatically identify locations where to order the candidate drugs, provide information indicating the locations to the user device, and allow the user of the user device to order the candidate drugs from the locations or request that the candidate drugs be automatically ordered from the locations; automatically identify doctors specializing in the treatment of SARS Type B; automatically make an appointment for the user of the user device with one of the identified doctors; provide information indicating the identified doctors to the user of user device, and allow the user of the user device to make an appointment with one of the identified doctors or request that the appointment be automatically made for the user; and/or the like.

As shown in FIG. 1H, and by reference number 150, the prediction platform may determine, based on the knowledge graph and a result for a particular candidate drug (e.g., "Drug 1 has effect on SARS Type B," and a score of 0.85), a neighborhood of the particular candidate drug (e.g., Drug 1). In some implementations, the prediction platform may determine the neighborhood of the particular candidate drug by sampling the neighborhood of the particular candidate drug in the knowledge graph, and determining whether the neighborhood preserves a fidelity of a description of the particular candidate drug. In such implementations, the prediction platform may determine whether the neighborhood preserves the fidelity of the description of the particular candidate drug based on whether knowledge graph embeddings of the neighborhood, described below, explain the score of the particular candidate drug.

In some implementations, the prediction platform may utilize one or more neighborhood sampling techniques to determine the neighborhood of the particular candidate drug, such as an exhaustive technique, a random walk technique, a graph-traversal technique, a degree-based technique, an evolutionary technique, and/or the like.

The exhaustive technique may include a sampling technique in which all available neighborhoods are sampled. For example, for a sample of three-hundred concepts, in order to be sure that each neighborhood is proportionately represented, ten concepts may be randomly selected from each neighborhood. However, if some neighborhoods are larger than others, the numbers sampled from each neighborhood may be made proportional to neighborhood size.

The random walk technique may include a neighborhood sampling technique that employs a random walk. A random walk may include a mathematical object, known as a stochastic or random process, which describes a path that includes a succession of random steps on a mathematical space. For example, the random walk technique may randomly select an initial node of the knowledge graph, then select a neighbor of the initial node as a visiting node, then select a neighbor of the visiting node, and continue the process with each next selected neighbor.

The graph-traversal technique may include a neighborhood sampling technique that randomly selects a seed node in a knowledge graph and then traverses neighboring nodes. For example, the graph traversal technique may include a breadth-first search (BFS) technique, a depth-first search (DFS) technique, a forest fire (FF) sampling technique, and/or a snowball sampling (SBS) technique. In some implementations, the BFS technique may select an earliest discovered but not yet visited node at each iteration, discovering all nodes within a particular distance from the seed node. In some implementations, the DFS technique may select a latest explored but not yet visited node at each iteration, first exploring nodes farther away from the seed node. In some implementations, the FF technique may include a randomized version of the BFS technique, where each neighbor of a current node is visited with a probability (e.g., less than one), thereby allowing the traversal to potentially end before all nodes are covered. In some implementations, the SBS technique may include a variation of the BFS technique in which, for each current node, not all neighbors of the current node are necessarily chosen, but neighbors (that have not been visited before) are chosen randomly.

The degree-based technique may include a neighborhood sampling technique that selects nodes in a knowledge graph based on degrees of the nodes. In this case, the degree of a node in a knowledge graph is the number of connections the node has to other nodes in the graph. For example, the degree-based technique may include a random degree node selection (RDN) in which a node, having a higher degree than other nodes, has a higher chance to be selected than the other nodes.

The evolutionary technique may include a neighborhood sampling technique that employs an evolutionary algorithm. An evolutionary algorithm attempts to solve a potentially complex problem by mimicking the process of Darwinian evolution. For example, in the evolutionary technique, a number of artificial entities may search over the space of the problem. The artificial entities compete continually with each other to discover optimal areas of the search space, with the objective that the most successful of the entities will discover an optimal solution.

In this way, the prediction platform may utilize one or more of the neighborhood sampling techniques to determine the neighborhood of the particular candidate drug. In some implementations, the prediction platform may select which one or more of the neighborhood sampling techniques to utilize based on the subject of the ontology. In some implementations, the prediction platform may utilize multiple neighborhood sampling techniques, may weight results of the multiple neighborhood sampling techniques, and may combine the results to obtain a final result (e.g., the neighborhood of the particular candidate drug).

As further shown in FIG. 1H, the neighborhood of the particular candidate drug may include a knowledge graph indicating that Drug 1 has an effect on SARS Type B, and is a treatment; that a vaccine is a treatment, and is a SARS vaccine; and that SARS Type B has a high fever as a symptom, affects the lungs, and is caused by Virus_XYZ. In some implementations, the neighborhood of the particular candidate drug may include more or less information than depicted in FIG. 1H.

As shown in FIG. 1I, and by reference number 155, the fit/train engine, of the prediction platform, may generate knowledge graph embeddings for the neighborhood of the particular candidate drug. In some implementations, the knowledge graph embeddings for the neighborhood of the particular candidate drug may include points in a k-dimensional metric space, and may provide latent semantic representations for structured knowledge in the knowledge graph. In some implementations, the knowledge graph embeddings for the neighborhood of the particular candidate drug may enable direct explicit relational inferences among entities via simple calculation of embedding vectors, and may be effective at highlighting key concepts underlying sophisticated human language. In some implementations, the fit/train engine, of the prediction platform, may generate the knowledge graph embeddings for the neighborhood of the particular candidate drug in a manner similar to the manner described above, in connection with FIG. 1C, for the knowledge graph embeddings.

As further shown in FIG. 1I, the knowledge graph embeddings for the neighborhood of the particular candidate drug may indicate that Drug 1 has an effect on SARS Type B. In some implementations, the fit/train engine may generate knowledge graph embeddings (e.g., points) on a two-dimensional metric space. As further shown, the points may include a point representing Drug 1 (e.g., located at first particular coordinates), a point representing SARS Type B (e.g., located at second particular coordinates), and points (not labeled) representing other nodes of the neighborhood of the particular candidate drug (e.g., a point representing the treatment node, a point representing the vaccine node, a point representing the SARS vaccine node, a point representing the virus_XYZ node, a point representing the high fever node, and a point representing the lungs node).

As shown in FIG. 1J, and by reference number 160, the prediction platform may process the revised knowledge graph embeddings (e.g., described above in connection with to FIG. 1E) and the knowledge graph embeddings for the neighborhood of the particular candidate drug (e.g., described above in connection with FIG. 1I), with a loss of quality computation, to determine a particular neighborhood (e.g., a portion of the neighborhood) with a smallest loss of quality for the particular candidate drug. In some implementations, the loss of quality computation may include calculating a loss of quality $L_Q$ according to the equation $L_Q = 1 - Q_e$, where $0 \leq L_Q \leq 1$ and $Q_e$ corresponds to a quality value for embeddings. In such implementations, the loss of quality computation may include one or more of a Kruskal stress calculation, a Sammon stress calculation, a residual variance calculation, a relative error calculation, a normalization independent embedding quality assessment (NIEQA) calculation, and/or the like.

The Kruskal stress calculation may include an application of a Kruskal goodness-of-fit calculation to determine a neighborhood with the smallest loss of quality for the particular candidate drug. The Kruskal stress calculation may be defined as $$\sqrt{\frac{\sum (d_{ij} - \delta_{ij})^2}{\sum d_{ij}^2}},$$

where $d_{ij}$ represents distances, and $\delta_{ij}$ represents disparities.

The Sammon stress calculation may include a loss of quality computation that employs a Sammon mapping (or Sammon projection) to determine a neighborhood with the smallest loss of quality for the particular candidate drug. A Sammon mapping may include an algorithm that maps a high-dimensional space to a space of lower dimensionality by trying to preserve a structure of inter-point distances of the high-dimensional space in the lower-dimension projection.

The residual variance calculation may include a loss of quality computation that determines a residual variance (also called unexplained variance). A residual variance may be an observable estimate of an unobservable difference from an expected value. The residual variance may be the variance of such a residual. For example, the residual variance may be the variance $\sigma^2(y-Y)$ of the difference between any variate y and its regression function Y. A residual variance may be associated with a variation of a metric within a particular group (e.g., a variation of heights within a group of adult males).

The relative error calculation may include a loss of quality computation that determines an approximation error (e.g., a relative error). An approximation error may be associated with a discrepancy between an exact value and an approximation of the exact value. A relative error may be determined as an absolute error (e.g., a magnitude of a difference between the exact value and the approximation) divided by the magnitude of the exact value.

The NIEQA calculation may include an embedding quality assessment method for manifold learning. The NIEQA calculation is based on a measure which can effectively evaluate how well a local neighborhood geometry is preserved under normalization, and therefore can be applied to both isometric and normalized embeddings. The NIEQA calculation can provide both local and global evaluations to output an overall assessment. Therefore, the NIEQA calculation can serve as a natural tool in model selection and evaluation tasks for manifold learning.

In this way, the prediction platform may utilize one or more of the Kruskal stress calculation, the Sammon stress calculation, the residual variance calculation, the relative error calculation, the NIEQA calculation, and/or the like, to perform the loss of quality computation and to determine the particular neighborhood. In some implementations, the prediction platform may select which one or more of the calculations to utilize based on the subject of the ontology. In some implementations, the prediction platform may utilize multiple calculations, may weight results of the multiple calculations, and may combine the results to obtain a final result (e.g., the loss of quality computation to determine the particular neighborhood).

As further shown in FIG. 1J, the particular neighborhood with a smallest loss of quality for the particular candidate drug may include a knowledge graph indicating that Drug 1 has an effect on SARS Type B and is a treatment; and that SARS Type B affects the lungs and is caused by Virus_XYZ. In some implementations, the neighborhood with the smallest loss of quality may include less information than the neighborhood of the particular candidate drug, described above in connection with FIG. 1H.

As shown in FIG. 1K, and by reference numbers 110 and 165, the prediction platform may process the ontology and the particular neighborhood with the smallest loss of quality, with a reasoning model, to generate a reasoning graph for the particular candidate drug. In some implementations, the reasoning graph may include a knowledge graph that provides explanations of why the particular candidate drug (e.g., Drug 1) has an effect on SARS Type B and achieved a score of 0.85. In some implementations, the explanations provided in the reasoning graph may become more abstract (e.g., and less relevant) when moving in a particular direction (e.g., to the right) through the reasoning graph. In other words, a degree of abstraction of the explanations, in the reasoning graph, increases when moving to the right through the reasoning graph. Thus, the reasoning graph may be divided into levels of abstraction, with a first level of abstraction (e.g., less abstract and more relevant) being provided to the left of the dashed line in FIG. 1K and a second level of abstraction (e.g., more abstract and less relevant) being provided to the right of the dashed line in FIG. 1K. In some implementations, the reasoning graph may include two or more different levels of abstraction.

In some implementations, the reasoning model, utilized by the prediction platform to generate the reasoning graph, may include one or more of a resource description framework (RDF) model, a RDF schema (RDFS) model, a web ontology language (OWL) model, and/or the like.

The RDF model may be similar to classical conceptual modeling approaches, such as entity-relationship or class diagrams. The RDF model is based on making statements about resources in expressions of the form subject-predicate-object, known as triples. The subject denotes the resource, and the predicate denotes traits or aspects of the resource, and expresses a relationship between the subject and the object. For example, one way to represent a notion "The sky has the color blue," in the RDF model, is as the triple: a subject denoting "the sky," a predicate denoting "has the color," and an object denoting "blue." Therefore, the RDF model uses the subject instead of the object (or entity) in contrast to the typical approach of an entity-attribute-value model in object-oriented design (e.g., entity (sky), attribute (color), and value (blue)). The RDF model is an abstract model with several serialization formats (i.e., file formats), so the particular encoding for resources or triples varies from format to format.

The RDFS model may include a set of classes with certain properties that utilize the RDF model, and provide basic elements for descriptions of ontologies (e.g., RDF vocabularies) intended to structure RDF resources. The RDFS model provides a data modeling vocabulary for RDF data. The RDFS model is a semantic extension of RDF, and provides mechanisms for describing groups of related resources and relationships between the related resources. The RDFS model utilizes resources to determine characteristics of other resources, such as the domains and ranges of properties. The RDFS model, instead of defining a class in terms of properties of the class instances, describes properties in terms of classes of a resource to which the properties apply.

The OWL model may include a family of knowledge representation languages for authoring ontologies. Ontologies are a formal way to describe taxonomies and classification networks, essentially defining a structure of knowledge for various domains. Ontologies resemble class hierarchies in object-oriented programming but there are several differences. Class hierarchies represent structures used in source code that evolve fairly slowly, whereas ontologies represent information that is expected to be evolving almost constantly. Ontologies are typically far more flexible as the ontologies represent information derived from heterogeneous data sources. Class hierarchies, on the other, hand are fairly static and rely on far less diverse and more structured sources of data. The OWL model is characterized by formal semantics, and is built upon the resource description framework (RDF).

In this way, the prediction platform may utilize one or more of the reasoning models to generate the reasoning graph for the particular candidate drug. In some implementations, the prediction platform may select which one or more of the reasoning models to utilize based on the subject of the ontology. In some implementations, the prediction platform may utilize multiple reasoning models, may weight results of the multiple reasoning models, and may combine the results to obtain a final result (e.g., the reasoning graph for the particular candidate drug).

In some implementations, the reasoning graph may indicate (e.g., at the first level of abstraction) that Drug 1 fights against coronaviruses, SARS Type B is caused by virus_XYZ, and SARS Type B causes a high fever. In some implementations, the reasoning graph may indicate (e.g., at the second level of abstraction) virus_XYZ is a coronavirus, a coronavirus causes a high fever, and a coronavirus affects the lungs.

Figure 1L:
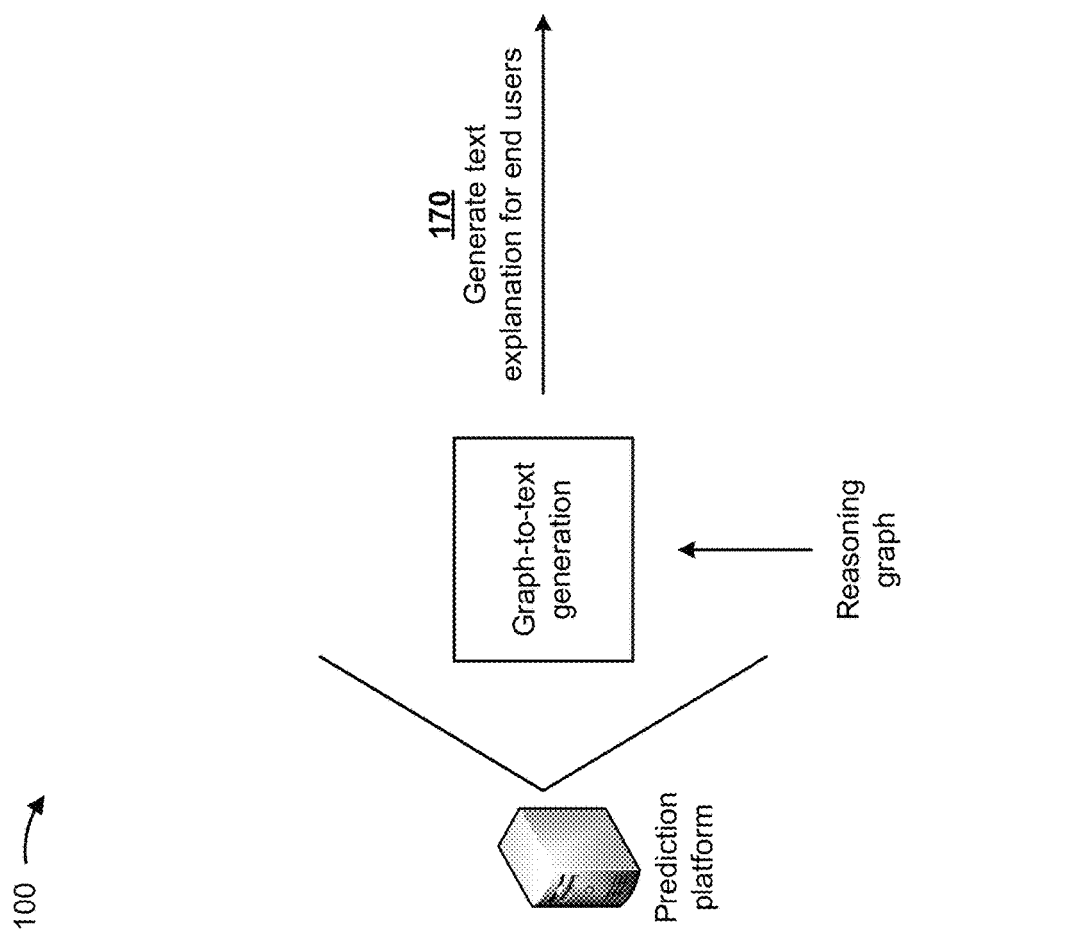

As shown in FIG. 1L, and by reference number 170, the prediction platform may generate, based on the reasoning graph, a text explanation (e.g., for end users) of why the particular candidate drug (e.g., Drug 1) has an effect on SARS Type B and achieved a score of 0.85. In some implementations, the prediction platform may convert the reasoning graph into the text explanation. In some implementations, the text explanation may include two or more different levels of abstraction, such as a first text explanation of the first level of abstraction of the reasoning graph, and a second text explanation of the second level of abstraction of the reasoning graph. For example, as shown in FIG. 1L, the text explanation may indicate that the "prediction that Drug 1 has an effect on SARS Type B (Score: 0.85) is because: (1) Drug 1 fights against coronaviruses, SARS Type B is caused by Virus_XYZ, and SARS Type B causes a high fever; and (2) Virus_XYZ is a coronavirus, a coronavirus causes a high fever, and a coronavirus affects the lungs."

In some implementations, the prediction platform may perform a variety of actions based on the text explanation and/or the particular candidate drug. For example, the prediction platform may automatically order the particular candidate drug if there is an uptick in SARS Type B; may automatically identify locations where to order the particular candidate drug, provide information indicating the locations to the user device, and allow the user of the user device to order the particular candidate drug from the locations or request that the particular candidate drug be automatically ordered from the locations; may automatically identify doctors specializing in the treatment of SARS Type B; may automatically make an appointment for the user of the user device with one of the identified doctors; may provide information indicating the identified doctors to the user of user device, and allow the user of the user device to make an appointment with one of the identified doctors or request that the appointment be automatically made for the user; and/or the like. In another example, the prediction platform may provide the text explanation to the user device, and the user device may display the text explanation to a user of the user device (e.g., via a user interface).

In this way, several different stages of the process for determining explanations for predicted links in knowledge graphs are automated, which may remove human subjectivity and waste from the process, and which may improve speed and efficiency of the process and conserve computing resources (e.g., processing resources, memory resources, and/or the like). Furthermore, implementations described herein use a rigorous, computerized process to perform tasks or roles that were not previously performed or were previously performed using subjective human intuition or input. For example, currently there does not exist a technique to determine explanations for predicted links in knowledge graphs. Finally, automating the process for determining explanations for predicted links in knowledge graphs conserves computing resources (e.g., processors, memory, and/or the like) that would otherwise be wasted in attempting to determine explanations for predicted links in knowledge graphs.

As indicated above, FIGS. 1A-1L are provided merely as examples. Other examples are possible and may differ from what was described with regard to FIGS. 1A-1L.

Figure 2:
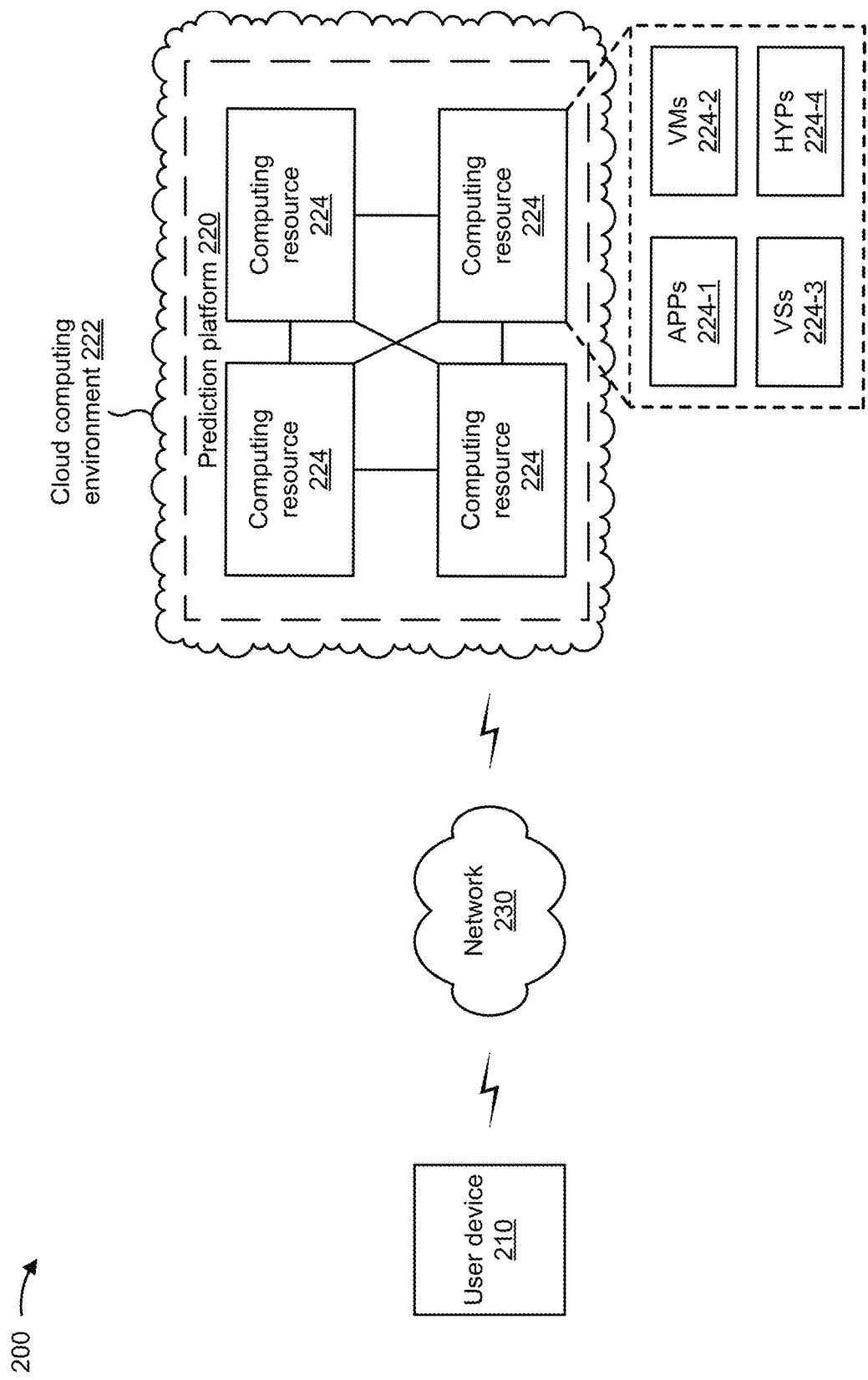
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a user device 210, a prediction platform 220, and a network 230. Devices of environment 200 may interconnect via wired connections, wireless connections, or a combination of wired and wireless connections.

User device 210 includes one or more devices capable of receiving, generating, storing, processing, and/or providing information, such as information described herein. For example, user device 210 may include a mobile phone (e.g., a smart phone, a radiotelephone, etc.), a laptop computer, a tablet computer, a desktop computer, a handheld computer, a gaming device, a wearable communication device (e.g., a smart wristwatch, a pair of smart eyeglasses, etc.), or a similar type of device. In some implementations, user device 210 may receive information from and/or transmit information to prediction platform 220.

Prediction platform 220 includes one or more devices that determine explanations for predicted links in knowledge graphs. In some implementations, prediction platform 220 may be designed to be modular such that certain software components may be swapped in or out depending on a particular need. As such, prediction platform 220 may be easily and/or quickly reconfigured for different uses. In some implementations, prediction platform 220 may receive information from and/or transmit information to one or more user devices 210.

In some implementations, as shown, prediction platform 220 may be hosted in a cloud computing environment 222. Notably, while implementations described herein describe prediction platform 220 as being hosted in cloud computing environment 222, in some implementations, prediction platform 220 may not be cloud-based (i.e., may be implemented outside of a cloud computing environment) or may be partially cloud-based.

Cloud computing environment 222 includes an environment that hosts prediction platform 220. Cloud computing environment 222 may provide computation, software, data access, storage, etc. services that do not require end-user knowledge of a physical location and configuration of system(s) and/or device(s) that hosts prediction platform 220. As shown, cloud computing environment 222 may include a group of computing resources 224 (referred to collectively as "computing resources 224" and individually as "computing resource 224").

Computing resource 224 includes one or more personal computers, workstation computers, server devices, or other types of computation and/or communication devices. In some implementations, computing resource 224 may host prediction platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, and/or the like.

Application 224-1 includes one or more software applications that may be provided to or accessed by user device 210. Application 224-1 may eliminate a need to install and execute the software applications on user device 210. For example, application 224-1 may include software associated with prediction platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system ("OS"). A process virtual machine may execute a single program, and may support a single process. In some implementations, virtual machine 224-2 may execute on behalf of a user (e.g., a user of user device 210 or an operator of prediction platform 220), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems, and may manage the execution of the guest operating systems. Multiple instances of a variety of operating systems may share virtualized hardware resources.

Network 230 includes one or more wired and/or wireless networks. For example, network 230 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, and/or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
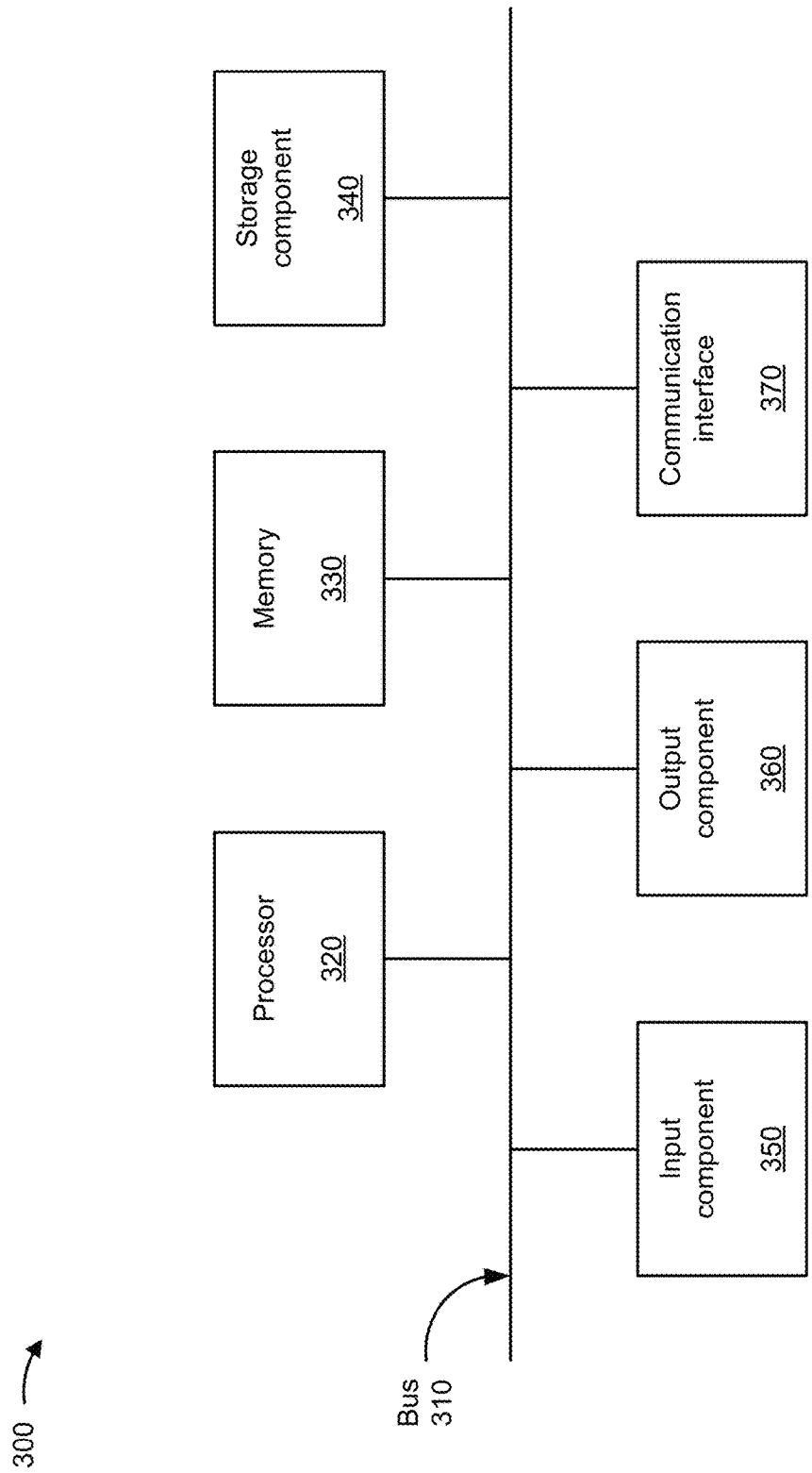
FIG. 3 is a diagram of example components of one or more devices of FIG. 2.

FIG. 3 is a diagram of example components of a device 300. Device 300 may correspond to user device 210, prediction platform 220, and/or computing resource 224. In some implementations, user device 210, prediction platform 220, and/or computing resource 224 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
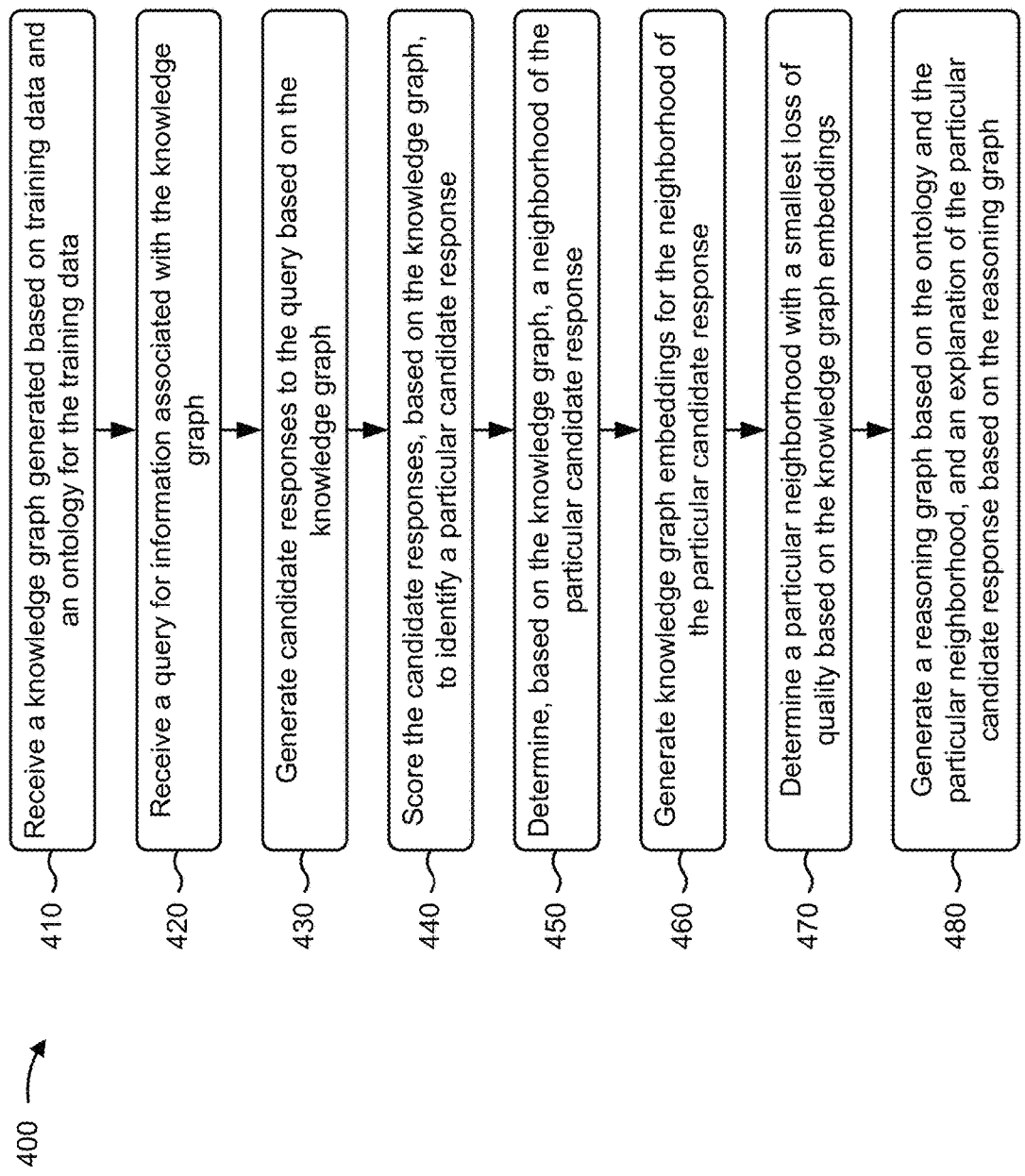
FIG. 4 is a flow chart of an example process for determining explanations for predicted links in knowledge graphs.

FIG. 4 is a flow chart of an example process 400 for determining explanations for predicted links in knowledge graphs. In some implementations, one or more process blocks of FIG. 4 may be performed by prediction platform 220. In some implementations, one or more process blocks of FIG. 4 may be performed by another device or a group of devices separate from or including prediction platform 220, such as user device 210.

As shown in FIG. 4, process 400 may include receiving a knowledge graph generated based on training data and an ontology for the training data (block 410). For example, prediction platform 220 (e.g., using computing resource 224, processor 320, memory 330, storage component 340, and/or the like) may receive a knowledge graph generated based on training data and an ontology for the training data, as described above in connection with FIGS. 1A-2.

As further shown in FIG. 4, process 400 may include receiving a query for information associated with the knowledge graph (block 420). For example, prediction platform 220 (e.g., using computing resource 224, processor 320, communication interface 370, and/or the like) may receive a query for information associated with the knowledge graph, as described above in connection with FIGS. 1A-2.

As further shown in FIG. 4, process 400 may include generating candidate responses to the query based on the knowledge graph (block 430). For example, prediction platform 220 (e.g., using computing resource 224, processor 320, memory 330, storage component 340, and/or the like) may generate candidate responses to the query based on the knowledge graph, as described above in connection with FIGS. 1A-2.

As further shown in FIG. 4, process 400 may include scoring the candidate responses, based on the knowledge graph, to identify a particular candidate response (block 440). For example, prediction platform 220 (e.g., using computing resource 224, processor 320, memory 330, and/or the like) may score the candidate responses, based on the knowledge graph, to identify a particular candidate response, as described above in connection with FIGS. 1A-2.

As further shown in FIG. 4, process 400 may include determining, based on the knowledge graph, a neighborhood of the particular candidate response (block 450). For example, prediction platform 220 (e.g., using computing resource 224, processor 320, storage component 340, and/or the like) may determine, based on the knowledge graph, a neighborhood of the particular candidate response, as described above in connection with FIGS. 1A-2.

As further shown in FIG. 4, process 400 may include generating knowledge graph embeddings for the neighborhood of the particular candidate response (block 460). For example, prediction platform 220 (e.g., using computing resource 224, processor 320, memory 330, and/or the like) may generate knowledge graph embeddings for the neighborhood of the particular candidate response, as described above in connection with FIGS. 1A-2.

As further shown in FIG. 4, process 400 may include determining a particular neighborhood with a smallest loss of quality based on the knowledge graph embeddings (block 470). For example, prediction platform 220 (e.g., using computing resource 224, processor 320, storage component 340, and/or the like) may determine a particular neighborhood with a smallest loss of quality based on the knowledge graph embeddings, as described above in connection with FIGS. 1A-2.

As further shown in FIG. 4, process 400 may include generating a reasoning graph based on the ontology and the particular neighborhood, and an explanation of the particular candidate response based on the reasoning graph (block 480). For example, prediction platform 220 (e.g., using computing resource 224, processor 320, memory 330, storage component 340, and/or the like) may generate a reasoning graph based on the ontology and the particular neighborhood, and an explanation of the particular candidate response based on the reasoning graph, as described above in connection with FIGS. 1A-2.

Process 400 may include additional implementations, such as any single implementation or any combination of implementations described below and/or described with regard to any other process described herein.

In some implementations, the reasoning graph may receive an embedding with a predicted link, and, when determining the particular neighborhood with the smallest loss of quality, may compare a quality of the knowledge graph embeddings for the neighborhood relative to the received embedding, and may determine the particular neighborhood with the smallest loss of quality based on comparing the quality of the knowledge graph embeddings. In some implementations, the prediction platform, when performing the action, may provide information identifying the particular candidate response and the explanation of the particular candidate response. In some implementations, the prediction platform, when determining the neighborhood of the particular candidate response, may select a neighborhood sampling technique, from multiple neighborhood sampling techniques, to determine the neighborhood of the particular candidate response, where the multiple neighborhood sampling techniques includes an exhaustive technique, a random walk technique, a graph-traversal technique, a degree-based technique, and an evolutionary technique.

In some implementations, the prediction platform, when determining the particular neighborhood with the smallest loss of quality, may utilize a loss of quality computation to determine the particular neighborhood with the smallest loss of quality, wherein the loss of quality computation may include one or more of a Kruskal stress calculation, a Sammon stress calculation, a residual variance calculation, a relative error calculation, or a NIEQA calculation. In some implementations, the explanation of the particular candidate response may include two or more different levels of abstraction associated with the explanation. In some implementations, the prediction platform, when determining the particular neighborhood with the smallest loss of quality, may select a neighborhood sampling technique, from a plurality of neighborhood sampling techniques, and may determine the particular neighborhood with the smallest loss of quality based on the selected neighborhood sampling technique.

In some implementations, the prediction platform, when generating the reasoning graph, may process the ontology and the portion of the neighborhood, with a reasoning model, to generate the reasoning graph, wherein the reasoning model may include one or more of a RDF model, a RDFS model, or an OWL model. In some implementations, the prediction platform may utilize a relational learning model to determine values associated with the candidate responses, and may utilize the values to score the candidate responses.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Some implementations described herein provide a prediction platform that determines explanations for predicted links in knowledge graphs. For example, the prediction platform may receive a knowledge graph generated based on training data and an ontology for the training data, and may receive a query for information associated with the knowledge graph. The prediction platform may generate candidate responses to the query based on the knowledge graph, and may score the candidate responses based on the knowledge graph. The prediction platform may determine, based on the knowledge graph, a neighborhood of the particular candidate response, and may generate knowledge graph embeddings for the neighborhood of the particular candidate response. The prediction platform may determine a particular neighborhood with a smallest loss of quality based on the knowledge graph embeddings. The prediction platform may generate a reasoning graph based on the ontology and the particular neighborhood, and may generate an explanation of the particular candidate response based on the reasoning graph.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

Certain user interfaces have been described herein and/or shown in the figures. A user interface may include a graphical user interface, a non-graphical user interface, a text-based user interface, or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A device, comprising:
one or more memories; and
one or more processors, communicatively coupled to the one or more memories, to:
receive a knowledge graph and an ontology for the knowledge graph;
receive a query for information associated with the knowledge graph;
generate candidate responses to the query based on the knowledge graph;
assign scores to the candidate responses based on the knowledge graph;
identify a particular candidate response, of the candidate responses, based on the scores for the candidate responses;
determine, based on the knowledge graph, a neighborhood of the particular candidate response;
generate knowledge graph embeddings for the neighborhood of the particular candidate response;
determine a subset of the neighborhood, with a smallest loss of quality, based on the knowledge graph embeddings;
generate a reasoning graph based on the ontology and the subset of the neighborhood,
wherein the reasoning graph includes a first level of abstraction and a second level of abstraction,
wherein the first level of abstraction and the second level of abstraction are determined based on a degree of abstraction that increases when moving in a particular direction through the reasoning graph;
generate an explanation of and an achieved score associated with the particular candidate response based on the reasoning graph; and
perform an action based the explanation of the particular candidate response.

2. The device of claim 1, wherein the one or more processors are further to:
receive an embedding with a predicted link, and
wherein the one or more processors, when determining the subset of the neighborhood with the smallest loss of quality, are to:
compare a quality of the knowledge graph embeddings for the neighborhood relative to the received embedding; and
determine the subset of the neighborhood with the smallest loss of quality based on comparing the quality of the knowledge graph embeddings.

3. The device of claim 1, wherein the one or more processors, when performing the action, are to:
provide information identifying the particular candidate response and the explanation of the particular candidate response.

4. The device of claim 1, wherein the one or more processors, when determining the neighborhood of the particular candidate response, are to:
select a neighborhood sampling technique, from a plurality of neighborhood sampling techniques, to determine the neighborhood of the particular candidate response,
wherein the plurality of neighborhood sampling techniques includes:
an exhaustive technique,
a random walk technique,
a graph-traversal technique,
a degree-based technique, and
an evolutionary technique.

5. The device of claim 1, wherein the one or more processors, when determining the subset of the neighborhood with the smallest loss of quality, are to:
utilize a loss of quality computation to determine the subset of the neighborhood with the smallest loss of quality,
wherein the loss of quality computation includes one or more of:
a Kruskal stress calculation,
a Sammon stress calculation,
a residual variance calculation,
a relative error calculation, or
a normalization independent embedding quality assessment (NIEQA) calculation.

6. The device of claim 1, wherein the explanation of the particular candidate response includes two or more different levels of abstraction associated with the explanation.

7. The device of claim 1, wherein the one or more processors, when determining the subset of the neighborhood with the smallest loss of quality, are to:
select a neighborhood sampling technique, from a plurality of neighborhood sampling techniques; and
determine the subset of the neighborhood with the smallest loss of quality based on the selected neighborhood sampling technique.

8. A non-transitory computer-readable medium storing instructions, the instructions comprising:
one or more instructions that, when executed by one or more processors, cause the one or more processors to:
receive a knowledge graph generated based on training data and an ontology for the training data,
the training data including information associated with a subject of the ontology;
receive a query for information associated with the knowledge graph;
generate candidate responses to the query based on the knowledge graph;
identify a particular candidate response, of the candidate responses, based on scoring the candidate responses based on the knowledge graph;
determine, based on the knowledge graph, a neighborhood of the particular candidate response;
generate knowledge graph embeddings for the neighborhood of the particular candidate response;
identify, based on the knowledge graph embeddings, a portion of the neighborhood with a smallest loss of quality;
generate a reasoning graph based on the ontology and the portion of the neighborhood, wherein the reasoning graph includes a first level of abstraction and a second level of abstraction,
wherein the first level of abstraction and the second level of abstraction are determined based on a degree of abstraction that increases when moving in a particular direction through the reasoning graph;
generate an explanation of and an achieved score associated with the particular candidate response based on the reasoning graph; and
perform one or more actions based the explanation of the particular candidate response.

9. The non-transitory computer-readable medium of claim 8, wherein the one or more instructions, that cause the one or more processors to perform the one or more actions, cause the one or more processors to:
provide, for display, information identifying the particular candidate response and the explanation of the particular candidate response.

10. The non-transitory computer-readable medium of claim 8, wherein the one or more instructions, that cause the one or more processors to generate the reasoning graph, cause the one or more processors to:
process the ontology and the portion of the neighborhood, with a reasoning model, to generate the reasoning graph,
wherein the reasoning model includes one or more of:
a resource description framework (RDF) model,
a RDF schema (RDFS) model, or
a web ontology language (OWL) model.

11. The non-transitory computer-readable medium of claim 8, wherein the one or more instructions, that cause the one or more processors to determine the neighborhood of the particular candidate response, cause the one or more processors to:
utilize one or more neighborhood sampling techniques to determine the neighborhood of the particular candidate response.

12. The non-transitory computer-readable medium of claim 8, wherein the one or more instructions, that cause the one or more processors to identify the portion of the neighborhood with the smallest loss of quality, cause the one or more processors to:
utilize a loss of quality computation to identify the portion of the neighborhood with the smallest loss of quality.

13. The non-transitory computer-readable medium of claim 8, wherein the explanation of the particular candidate response includes two or more different levels of abstraction associated with the explanation.

14. The non-transitory computer-readable medium of claim 8, wherein the instructions further comprise:
one or more instructions that, when executed by the one or more processors, cause the one or more processors to:
utilize a relational learning model to determine values associated with the candidate responses; and
utilize the values to score the candidate responses.

15. A method, comprising:
receiving, by a device, a knowledge graph generated based on training data and an ontology for the training data;
receiving, by the device, a query for information associated with the knowledge graph;
generating, by the device, candidate responses to the query based on the knowledge graph;
assigning, by the device, scores to the candidate responses based on the knowledge graph;
identifying, by the device, a particular candidate response, of the candidate responses, based on the scores for the candidate responses;
determining, by the device and based on the knowledge graph, a neighborhood of the particular candidate response;
generating, by the device, knowledge graph embeddings for the neighborhood of the particular candidate response,
the knowledge graph embeddings including points in a k-dimensional metric space;
identifying, by the device and based on the knowledge graph embeddings, a portion of the neighborhood with a smallest loss of quality;
generating, by the device, a reasoning graph based on the ontology and the portion of the neighborhood,
the reasoning graph including two or more different levels of abstraction associated with nodes that represent concepts and links that represent relations between the concepts,
wherein a first level of abstraction, of the two or more different levels of abstraction, and a second level of abstraction, of the two or more different levels of abstraction, are determined based on a degree of abstraction that increases when moving in a particular direction through the reasoning graph;
generating, by the device, an explanation of and an achieved score associated with the particular candidate response based on the reasoning graph; and
performing, by the device, at least one action based the explanation of the particular candidate response.

16. The method of claim 15, wherein determining the neighborhood of the particular candidate response comprises:
processing the knowledge graph, with one or more neighborhood sampling techniques, to determine the neighborhood of the particular candidate response,
wherein the one or more neighborhood sampling techniques include one or more of:
an exhaustive technique,
a random walk technique,
a graph-traversal technique,
a degree-based technique, or
an evolutionary technique.

17. The method of claim 15, wherein identifying the portion of the neighborhood with the smallest loss of quality comprises:
processing the knowledge graph embeddings, with a loss of quality computation, to determine the portion of the neighborhood with the smallest loss of quality,
wherein the loss of quality computation includes one or more of:
a Kruskal stress calculation,
a Sammon stress calculation,
a residual variance calculation,
a relative error calculation, or
a normalization independent embedding quality assessment (NIEQA) calculation.

18. The method of claim 15, wherein the explanation of the particular candidate response includes the two or more different levels of abstraction,
the two or more different levels of abstraction being associated with the explanation.

19. The method of claim 15, wherein performing the at least one action comprises:

providing, for display, information identifying the particular candidate response and the explanation of the particular candidate response.

20. The method of claim 15, wherein generating the reasoning graph comprises:
processing the ontology and the portion of the neighborhood, with a reasoning model, to generate the reasoning graph,
wherein the reasoning model includes one or more of:
a resource description framework (RDF) model,
a RDF schema (RDFS) model, or
a web ontology language (OWL) model.

* * * * *